US006515005B2

(12) United States Patent
Dubowchik et al.

(10) Patent No.: US 6,515,005 B2
(45) Date of Patent: Feb. 4, 2003

(54) SUBSTITUTED AZOLE DERIVATIVES AS INHIBITORS OF CORTICOTROPIN RELEASING FACTOR

(75) Inventors: Gene M. Dubowchik, Middlefield, CT (US); Dmitry S. Zuev, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/954,137

(22) Filed: Sep. 17, 2001

(65) Prior Publication Data

US 2002/0161019 A1 Oct. 31, 2002

Related U.S. Application Data

(60) Provisional application No. 60/310,324, filed on Aug. 6, 2001, provisional application No. 60/256,993, filed on Dec. 20, 2000, provisional application No. 60/250,919, filed on Dec. 1, 2000, and provisional application No. 60/234,139, filed on Sep. 21, 2000.

(51) Int. Cl.$^7$ ............... C07D 263/48; A61K 31/421
(52) U.S. Cl. ............... 514/370; 514/377; 546/270.7; 548/194; 548/198; 548/234
(58) Field of Search ............... 548/234, 198, 548/194; 514/370, 377; 546/270.7

(56) References Cited

U.S. PATENT DOCUMENTS

| | | | |
|---|---|---|---|
| 2,636,037 A | | 4/1953 | Sprague et al. |
| 3,725,427 A | * | 4/1973 | Harrison ............... 548/190 |
| 4,735,957 A | | 4/1988 | Takaya et al. |

FOREIGN PATENT DOCUMENTS

| | | |
|---|---|---|
| EP | 0 773 023 A1 | 5/1997 |
| WO | WO 95/10506 | 4/1995 |
| WO | WO 95/33750 | 12/1995 |
| WO | WO 97/14684 | 4/1997 |
| WO | WO 97/35580 | 10/1997 |
| WO | WO 98/11075 | 3/1998 |
| WO | WO 98/42699 | 10/1998 |
| WO | WO 99/01439 | 1/1999 |
| WO | WO 00/62778 | 10/2000 |

OTHER PUBLICATIONS

Yamamoto. Chem Pharm Bull 32(11) 4292–99 1984.*
Nayak, J Indian Chem Soc 63 (11) 986–8 1986.*
Dunn, et al., "Physiological and behavioral response to corticotropin–releasing factor administration: is CRF a mediator of anxiety or stress responses?", Brain Research Reviews, 15, 1990, pp. 71–100.
Gulyas, et al., "Potent, structurally constrained agonists and competitive antagonists of corticotropin–releasing factor," Prac. Natl. Acad. Sci. USA, 92, 1995, pp. 10575–10579.
McCarthy, et al., "Recent Advances with the CRF1 Receptor: Design of Small Molecule Inhibitors, Receptor Subtypes and Clinical Indications," Current Pharmaceutical Design, 5, 1999, pp. 289–315.
Holsboer, "The rationale for corticotropin–releasing hormone receptor (CRH–R) antagonists to treat depression and anxiety," Journal of Psychiatric Research, 33, 1999, pp. 181–214.
Banki, et al., "CSF corticotropin–releasing hormone and somatostatin in major depression: response to antidepressant treatment and relapse," European Neuropsychopharmacology, 2, 1992, pp. 107–113.
Webster, et al., "Corticotropin–Releasing Hormone and Inflammation," Annals New York Academy of Sciences, 840, 1998, pp. 21–62.
Gilligan, et al., "Corticotropin Releasing Factor (CRF) Receptor Modulators: Progress and Opportunities for New Therapeutic Agents," Journal of Medicinal Chemistry, 43, 9, 2000, pp. 1641–1660.
McCarthy, et al., "Chapter 2. Recent Progress in Corticotropin–Releasing Factor Receptor Agents," Annual Reports in Medicinal Chemistry, 34, 1999, pp. 11–20.

* cited by examiner

*Primary Examiner*—Robert Gerstl
(74) *Attorney, Agent, or Firm*—Shah R. Makujina

(57) ABSTRACT

The present invention relates to thiazoles, oxazoles, imidazoles and pharmaceutical compositions comprising said compounds antagonizing the corticotropin releasing factor receptor ("CRF receptor") and useful for the treatment of depression, anxiety, affective disorders, feeding disorders, post-traumatic stress disorder, headache, drug addiction, inflammatory disorders, drug or alcohol withdrawal symptoms and other conditions the treatment of which can be effected by the antagonism of the CRF-1 receptor.

21 Claims, No Drawings

SUBSTITUTED AZOLE DERIVATIVES AS INHIBITORS OF CORTICOTROPIN RELEASING FACTOR

CROSS REFERENCE TO RELATED APPLICATIONS

This non-provisional application claims priority from provisional application U.S. Ser. No. 60/234,139 filed Sep. 21, 2000; provisional application U.S. Ser. No. 60/250,919 filed Dec. 1, 2000; provisional application U.S. Ser. No. 60/256,993 filed Dec. 20, 2000; and provisional application U.S. Ser. No. 60/310,324 filed Aug. 6, 2001.

FIELD OF THE INVENTION

The present invention relates to thiazoles, oxazoles, imidazoles and pharmaceutical compositions comprising said compounds antagonizing the corticotropin releasing factor receptor ("CRF receptor") and useful for the treatment of depression, anxiety, affective disorders, feeding disorders, post-traumatic stress disorder, headache, drug addiction, inflammatory disorders, drug or alcohol withdrawal symptoms and other conditions the treatment of which can be effected by the antagonism of the CRF-1 receptor.

BACKGROUND OF THE INVENTION

It has been shown that the neuropeptide, corticotropin releasing factor ("CRF"), acting through its binding to the CRF-1 receptor, is a primary mediator of stress- and anxiety-related physiological responses in humans and other mammals by stimulating ACTH secretion from the anterior pituitary gland. See A. J. Dunn, et al., Brain Res. Rev., 15: 71–100 (1990). Antagonists of the CRF-1 receptor, both peptides (J. Gulyas, et al., Proc. Natl. Acad. Sci. U.S.A., 92: 10575–10579 (1995) and small molecules (J. R. McCarthy, et al., Curr. Pharm. Design, 5: 289–315 (1999), have demonstrated the ability to ameliorate the effects of stressful stimuli in several animal models. In addition, marked elevations of CRF in cerebrospinal fluid have been detected in a large portion of individuals diagnosed with major depression and anxiety disorders, and the levels correlate with severity of the disease. See F. Holsboer, J. Psychiatric Res., 33: 181–214 (1999). Following antidepressant treatment, the increased CRF levels observed in depressed patients were reduced. See C. M. Banki, et al., Eur. Neuropsychopharmacol., 2: 107–113 (1992). CRF has also been shown to be a key mediator of several immune system functions through its effect on glucocorticoid plasma levels. See E. L. Webster, et al., Ann. N.Y. Acad. Sci., 840: 21–62 (1998). Recent reviews of the activity of CRF-1 antagonists, P. J. Gilligan, et al., J. Med. Chem., 43: 1641–1660 (2000) and J. R. McCarthy, et al., Ann. Rep. Med. Chem., 34: 11–20 (1999) are incorporated herein by reference. There appears a need to discover novel small molecule CRF antagonists in order to treat a wide variety of human disorders including depression, anxiety, bipolar disorder, and other stress-related illnesses. See WO 95/10506, WO 95/33750, WO 97/14684, WO 97/35580, WO 98/11075, WO 98/42699, WO 99/01439 and EP 773023.

SUMMARY OF THE INVENTION

Thus according to a first embodiment of the first aspect of the present invention are provided compounds of Formula (I) and pharmaceutically acceptable salts and solvates thereof

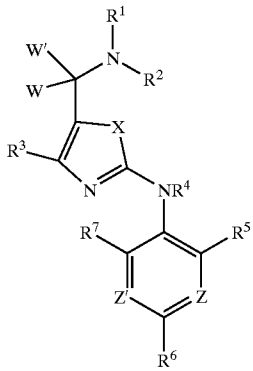

wherein
X is O, S, NH or N—$C_{1-6}$alkyl;
W and W' are each H or together are O or S;
Z and Z' are independently CH or N
provided that
if Z' is N, then Z is CH;
if Z is N, then Z' is CH;
$R^1$ and $R^2$ are each the same or different and selected from the group consisting of H, $C_{1-6}$alkyl, $C_{1-6}$haloalkyl, $C_{1-6}$alkoxy, $C_{3-7}$cycloalkyl, $C_{1-6}$alkyl-$C_{3-7}$cycloalkyl, $C_{2-6}$alkenyl, $C_{3-6}$alkynyl, $C_{1-6}$cyanoalkyl, $C_{1-6}$aralkyl, 5 or 6-membered heterocycle and 9 or 10-membered bicyclic fused heterocycle;
wherein
said $C_{1-6}$aralkyl is optionally substituted with one or more of the same or different halogens or with one or more of the same or different $C_{1-4}$alkoxy groups;
said 5 or 6-membered heterocycle contains one to three of the same or different heteroatoms selected from the group consisting of O, N and S and said 5 or 6-membered heterocycle is optionally substituted with $C_{1-4}$alkyl, $C_{1-4}$thioalkyl, $C_{1-4}$haloalkyl, halo, cyano or —O—$C_{1-4}$alkyl;
provided that if three of said heteroatoms are contained in said 5-membered heterocycle, said three heteroatoms are not all the same heteroatoms;
said 9 or 10-membered bicyclic fused heterocycle contains one to three of the same or different heteroatoms selected from the group consisting of O, N and S;
$R^1$ and $R^2$ together with the nitrogen to which they are attached form a five or six-membered heterocycle,
said heterocycle containing one to three of the same or different heteroatoms selected from the group consisting of N, S or O; and
said heterocycle optionally substituted with one or more $C_{1-6}$alkyl, —$C_{1-6}$alkyl-$C_{1-6}$alkoxy or $C_{1-6}$alkoxy groups;
$R^3$ is $C_{1-6}$alkyl, $C_{1-6}$haloalkyl, halo, cyano or $C_{1-6}$alkoxy;
$R^4$ is H or $C_{1-6}$alkyl; and
$R^5$, $R^6$ and $R^7$ are each the same or different and selected from the group consisting of H, $C_{1-6}$alkyl, $C_{1-6}$alkoxy, $C_{1-6}$thioalkyl, CN, $C_{1-6}$haloalkyl and halo.

According to another embodiment of the first aspect of the present invention are provided compounds of Formula (I) according to the first embodiment of the first aspect wherein said 5 or 6-membered heterocycle is pyridyl, pryrimidinyl, thienyl, imidazolyl, $C_{1-3}$thioalkyl-subsituted thiadiazolyl, pyrrolyl, pyrrolinyl, pyrrolidinyl, thiazolyl, oxazolyl or furanyl.

According to another embodiment of the first aspect of the present invention are provided compounds of Formula (I) according to the first embodiment of the first aspect wherein said 9 or 10-membered bicyclic fused heterocycle is benzofuranyl, indolyl, benzothiazolyl or benzimidazolyl.

According to another embodiment of the first aspect of the present invention are provided compounds of Formula (I) according to the first embodiment of the first aspect wherein $R^1$ is not H and $R^2$ is not H.

According to another embodiment of the first aspect of the present invention are provided compounds of Formula (I) according to the first embodiment of the first aspect wherein the optionally substituted heterocycle formed by $R^1$ and $R^2$ together with the nitrogen to which they are attached is selected from the group consisting pyrrolyl, pyrrolinyl, pyrrolidinyl, piperidinyl, piperazinyl, morpholinyl, imidazolyl and thiomorpholinyl.

According to another embodiment of the first aspect of the present invention are provided compounds of Formula (I) according to the first embodiment of the first aspect wherein $R^1$ and $R^2$ are each the same or different and selected from the group consisting of H, methyl, ethyl, propyl, isopropyl, cyclopropyl, propenyl, cyclopropylmethyl, butyl, n-butyl, sec-butyl, tert-butyl, cyclobutyl, pentyl, $(CH_2)_2CF_3$, $(CH_2)_2OCH_3$, $CH_2CH(CH_2CH_3)_2$, $CH_2CH(CH_2CH_3)(OCH_3)$, $CH_2CH(CH_3)_2$, $CH(CH_3)(CH_2CH_3)$, $CH_2CCH$, $CH_2CN$, $CH_2C(CH_2)(CH_3)$, $(CH_2)_2CN$, phenyl, methylphenyl, ethylphenyl, cyclobutylmethyl and propylphenyl.

According to another embodiment of the first aspect of the present invention are provided compounds of Formula (I) according to the first embodiment of the first aspect wherein $R^5$, $R^6$ and $R^7$ are each the same or different and selected from the group consisting of H, Br, Cl, methyl, isopropyl, $CF_3$ and methoxy.

According to another embodiment of the first aspect of the present invention are provided compounds of Formula (I) according to the first embodiment of the first aspect wherein $R^4$ is H.

According to another embodiment of the first aspect of the present invention are provided compounds of Formula (I) according to the first embodiment of the first aspect wherein $R^4$ is $CH_3$ or $CH_2CH_3$.

According to another embodiment of the first aspect of the present invention are provided compounds of Formula (I) according to the first embodiment of the first aspect wherein X is S.

According to another embodiment of the first aspect of the present invention are provided compounds of Formula (I) according to the first embodiment of the first aspect wherein X is O.

According to another embodiment of the first aspect of the present invention are provided compounds of Formula (I) according to the first embodiment of the first aspect wherein $R^3$ is $CF_3$.

According to another embodiment of the first aspect of the present invention are provided compounds of Formula (I) according to the first embodiment of the first aspect wherein $R^3$ is methyl, $R^4$ is H, $R^{5-7}$ are each chloro and X is S.

According to another embodiment of the first aspect of the present invention are provided compounds of Formula (I) according to the first embodiment of the first aspect wherein $R^3$ is methyl, $R^4$ is H, $R^{5-7}$ are each methyl and X is S.

According to another embodiment of the first aspect of the present invention are provided compounds of Formula (I) according to the first embodiment of the first aspect wherein W and W' together are O.

According to another embodiment of the first aspect of the present invention are provided compounds of Formula (I) according to the first embodiment of the first aspect wherein W and W' are each H.

According to another embodiment of the first aspect of the present invention are provided compounds of Formula (I) according to the first embodiment of the first aspect wherein W and W' are each H, $R^3$ is methyl, $R^4$ is H and X is S.

According to another embodiment of the first aspect of the present invention are provided compounds of Formula (I) according to the first embodiment of the first aspect wherein Z is N.

According to another embodiment of the first aspect of the present invention are provided compounds of Formula (I) according to the first embodiment of the first aspect wherein Z' is N.

According to another embodiment of the first aspect of the present invention are compounds of Formula (I) selected from the group consisting of 2-(2,4,6-Trimethylphenylamino)-5-(N-n-propyl-N-cyclopropylmethyl)aminomethyl-4-trifluoromethylthiazole; 2-(2-Chloro-4,6-dimethylphenylamino)-5-(N-n-propyl-N-cyclopropylmethyl)aminomethyl-4-trifluoromethylthiazole; 2-(2,4,6-Trichlorophenylamino)-5-(N-n-butyl-N-ethyl) aminomethyl-4-trifluoromethylthiazole; 2-(2,4,6-Trimethylphenylamino)-5-(N-n-butyl-N-ethyl) aminomethyl-4-trifluoromethylthiazole; 2-(2-Chloro-4,6-dimethylphenylamino)-5-(N-n-butyl-N-ethyl)aminomethyl-4-trifluoromethylthiazole; 2-(2,4,6-Trichlorophenylamino)-5-(N,N-bis-n-propyl)aminomethyl-4-trifluoromethylthiazole; 2-(2,4,6-Trimethylphenylamino)-5-(N,N-bis-n-propyl)aminomethyl-4-trifluoromethylthiazole; 2-(2-Chloro-4,6-dimethylphenylamino)-5-(N,N-bis-n-propyl)aminomethyl-4-trifluoromethylthiazole; 2-(2,4,6-Trichlorophenylamino)-5-(N,N-bis-2-methoxyethyl)aminomethyl-4-trifluoromethylthiazole; 2-(2,4,6-Trimethylphenylamino)-5-(N,N-bis-2-methoxyethyl)aminomethyl-4-trifluoromethylthiazole; 2-(2-Chloro-4,6-dimethylphenylamino)-5-(N,N-bis-2-methoxyethyl)aminomethyl-4-trifluoromethylthiazole; 2-(2,4,6-Trichlorophenylamino)-5-(N-2-methoxyethyl-N-ethyl)aminomethyl-4-trifluoromethylthiazole; 2-(2,4,6-Trimethylphenylamino)-5-(N-2-methoxyethyl-N-ethyl)aminomethyl-4-trifluoromethylthiazole; 2-(2-Chloro-4,6-dimethylphenylamino)-5-(N-2-methoxyethyl-N-ethyl)aminomethyl-4-trifluoromethylthiazole; 2-(2,4,6-Trichlorophenylamino)-5-(N-n-propyl-N-cyclopropylmethyl)aminomethyl-4-trifluoromethyloxazole; 2-(2,4,6-Trimethylphenylamino)-5-(N-n-propyl-N-cyclopropylmethyl)aminomethyl-4-trifluoromethyloxazole; 2-(2-Chloro-4,6-dimethylphenylamino)-5-(N-n-propyl-N-cyclopropylmethyl)aminomethyl-4-trifluoromethyloxazole; 2-(2,4,6-Trichlorophenylamino)-5-(N-n-butyl-N-ethyl) aminomethyl-4-trifluoromethyloxazole; 2-(2,4,6-Trimethylphenylamino)-5-(N-n-butyl-N-ethyl) aminomethyl-4-trifluoromethyloxazole; 2-(2-Chloro-4,6-dimethylphenylamino)-5-(N-n-butyl-N-ethyl)aminomethyl-4-trifluoromethyloxazole; 2-(2,4,6-Trichlorophenylamino)-5-(N,N-bis-n-propyl)aminomethyl-4-trifluoromethyloxazole; 2-(2,4,6-Trimethylphenylamino)-5-(N,N-bis-n-propyl)aminomethyl-4-trifluoromethyloxazole; 2-(2-Chloro-4,6-dimethylphenylamino)-5-(N,N-bis-n-propyl)aminomethyl-4-trifluoromethyloxazole; 2-(2,4,6-Trichlorophenylamino)-5-(N,N-bis-2-methoxyethyl) aminomethyl-4-trifluoromethyloxazole; 2-(2,4,6-Trimethylphenylamino)-5-(N,N-bis-2-methoxyethyl) aminomethyl-4-trifluoromethyloxazole; 2-(2-Chloro-4,6-dimethylphenylamino)-5-(N,N-bis-2-methoxyethyl) aminomethyl-4-trifluoromethyloxazole; 2-(2,4,6-

Trichlorophenylamino)-5-(N-2-methoxyethyl-N-ethyl)aminomethyl-4-trifluoromethyloxazole; 2-(2,4,6-Trimethylphenylamino)-5-(N-2-methoxyethyl-N-ethyl)aminomethyl-4-trifluoromethyloxazole; and 2-(2-Chloro-4,6-dimethylphenylamino)-5-(N-2-methoxyethyl-N-ethyl)aminomethyl-4-trifluoromethyloxazole.

According to another embodiment of the first aspect of the present invention are compounds of Formula (I) selected from the group consisting of (5-{[(4-Chlorobenzyl)-propyl-amino]-methyl}-4-trifluoromethylthiazol-2-yl)-(2,4,6-trichlorophenyl)-amine; (5-{[(3-Fluorobenzyl)-(3,3,3-trifluoropropyl)-amino]-methyl}-4-trifluoromethylthiazol-2-yl)-(2,4,6-trichlorophenyl)-amine; (5-{[(4-Fluorobenzyl)-(3,3,3-trifluoropropyl)-amino]-methyl}-4-trifluoromethylthiazol-2-yl)-(2,4,6-trichlorophenyl)-amine and (5-{[Benzyl-(3,3,3-trifluoropropyl)-amino]-methyl}-4-trifluoromethylthiazol-2-yl)-(2,4,6-trichlorophenyl)-amine.

According to another embodiment of the first aspect of the present invention are compounds of Formula (I) selected from the group consisting of (5-{[Benzyl-(3,3,3-trifluoropropyl)-amino]-methyl}-4-trifluoromethylthiazol-2-yl)-(2,4,6-trichlorophenyl)-amine; (5-{[(4-Chlorobenzyl)-propyl-amino]-methyl}-4-trifluoromethylthiazol-2-yl)-(2,4,6-trichlorophenyl)-amine; {5-[(Cyclopropylmethyl-ethyl-amino)-methyl]-4-trifluoromethyl-thiazol-2-yl}-(2,4,6-trichloro-phenyl)-amine; {5-[(Bis-cyclopropylmethyl-amino)-methyl]-4-trifluoromethyl-thiazol-2-yl}-(2,4,6-trichloro-phenyl)-amine; (5-{[(3,4-Dichloro-benzyl)-propyl-amino]-methyl}-4-trifluoromethyl-thiazol-2-yl)-(2,4,6-trichloro-phenyl)-amine (5-{[(4-Methoxy-benzyl)-propyl-amino]-methyl}-4-trifluoromethyl-thiazol-2-yl)-(2,4,6-trichloro-phenyl)-amine; {5-[(Benzyl-propyl-amino)-methyl]-4-trifluoromethyl-thiazol-2-yl}-(2,4,6-trichloro-phenyl)-amine; (5-{[Cyclopropylmethyl-(2,2,2-trifluoro-ethyl)-amino]-methyl}-4-trifluoromethyl-thiazol-2-yl)-(2,4,6-trichloro-phenyl)-amine; (5-{[Cyclopropylmethyl-(3,3,3-trifluoro-propyl)-amino]-methyl}-4-trifluoromethyl-thiazol-2-yl)-(2,4,6-trichloro-phenyl)-amine; {5-[(Allyl-cyclopropylmethyl-amino)-methyl]-4-trifluoromethyl-thiazol-2-yl}-(2,4,6-trichloro-phenyl)-amine; (5-{[Phenethyl-(2,2,2-trifluoro-ethyl)-amino]-methyl}-4-trifluoromethyl-thiazol-2-yl)-(2,4,6-trichloro-phenyl)-amine; (5-{[(3,4-Difluoro-benzyl)-propyl-amino]-methyl}-4-trifluoromethyl-thiazol-2-yl)-(2,4,6-trichloro-phenyl)-amine; (5-Diallylaminomethyl-4-trifluoromethyl-thiazol-2-yl)-(2,4,6-trichloro-phenyl)-amine; (2,4,6-Trichloro-phenyl)-(5-{[(2,2,2-trifluoro-ethyl)-(3,3,3-trifluoro-propyl)-amino]-methyl}-4-trifluoromethyl-thiazol-2-yl)-amine; [5-({[2-(3,4-Dichloro-phenyl)-ethyl]-propyl-amino}-methyl)-4-trifluoromethyl-thiazol-2-yl]-(2,4,6-trichloro-phenyl)-amine; {5-[(Cyclobutylmethyl-propyl-amino)-methyl]-4-trifluoromethyl-thiazol-2-yl}-(2,4,6-trichloro-phenyl)-amine; {5-[(Cyclopropylmethyl-prop-2-ynyl-amino)-methyl]-4-trifluoromethyl-thiazol-2-yl}-(2,4,6-trichloro-phenyl)-amine; (5-{[Cyclobutylmethyl-(2,2,2-trifluoro-ethyl)-amino]-methyl}-4-trifluoromethyl-thiazol-2-yl)-(2,4,6-trichloro-phenyl)-amine; {5-[(Benzo[1,3]dioxol-5-ylmethyl-propyl-amino)-methyl]-4-trifluoromethyl-thiazol-2-yl}-(2,4,6-trichloro-phenyl)-amine; (5-{[Propyl-(3,3,3-trifluoro-propyl)-amino]-methyl}-4-trifluoromethyl-thiazol-2-yl)-(2,4,6-trichloro-phenyl)-amine; {5-[(Benzyl-ethyl-amino)-methyl]-4-trifluoromethyl-thiazol-2-yl}-(2,4,6-trichloro-phenyl)-amine; {5-[(Propyl-thiophen-2-ylmethyl-amino)-methyl]-4-trifluoromethyl-thiazol-2-yl}-(2,4,6-trichloro-phenyl)-amine; (5-{[Phenethyl-(3,3,3-trifluoro-propyl)-amino]-methyl}-4-trifluoromethyl-thiazol-2-yl)-(2,4,6-trichloro-phenyl)-amine; (5-{[Propyl-(2,2,2-trifluoro-ethyl)-amino]-methyl}-4-trifluoromethyl-thiazol-2-yl)-(2,4,6-trichloro-phenyl)-amine; {5-[(Ethyl-propyl-amino)-methyl]-4-trfluoromethyl-thiazol-2-yl}-(2,4,6-trichloro-phenyl)-amine; (5-Dipropylaminomethyl-4-trifluoromethyl-thiazol-2-yl)-(2,4,6-trichloro-phenyl)-amine; (5-{[Cyclopropylmethyl-(2,2,3,3,3-pentafluoro-propyl)-amino]-methyl}-4-trifluoromethyl-thiazol-2-yl)-(2,4,6-trichloro-phenyl)-amine; (5-{[(2-Cyclopropyl-ethyl)-(2,2,2-trifluoro-ethyl)-amino]-methyl}-4-trifluoromethyl-thiazol-2-yl)-(2,4,6-trichloro-phenyl)-amine; {5-[(Isobutyl-propyl-amino)-methyl]-4-trifluoromethyl-thiazol-2-yl}-(2,4,6-trichloro-phenyl)-amine; 3{-Butyl-[2-(2,4,6-trichloro-phenylamino)-4-trifluoromethyl-thiazol-5-ylmethyl]-amino}-propionitrile; {5-[(Butyl-ethyl-amino)-methyl]-4-trifluoromethyl-thiazol-2-yl}-(2,4,6-trichloro-phenyl)-amine; (5-Diethylaminomethyl-4-trifluoromethyl-thiazol-2-yl)-(2,4,6-trichloro-phenyl)-amine; (5-{[Ethyl-(2-methyl-allyl)-amino]-methyl}-4-trifluoromethyl-thiazol-2-yl)-(2,4,6-trichloro-phenyl)-amine {5-[(Ethyl-pyridin-4-ylmethyl-amino)-methyl]-4-trifluoromethyl-thiazol-2-yl}-(2,4,6-trichloro-phenyl)-amine (5-{[Benzyl-(2,2,2-trifluoro-ethyl)-amino]-methyl}-4-trifluoromethyl-thiazol-2-yl)-(2,4,6-trichloro-phenyl)-amine; (5-{[(2-Cyclopropyl-ethyl)-propyl-amino]-methyl}-4-trifluoromethyl-thiazol-2-yl)-(2,4,6-trichloro-phenyl)-amine; (5-{[Ethyl-(2-methoxy-ethyl)-amino]-methyl}-4-trifluoromethyl-thiazol-2-yl)-(2,4,6-trichloro-phenyl)-amine; {5-[(Diisobutylamino)-methyl]-4-trifluoromethyl-thiazol-2-yl}-(2,4,6-trichloro-phenyl)-amine; {Butyl-[2-(2,4,6-trichloro-phenylamino)-4-trifluoromethyl-thiazol-5-ylmethyl]-amino}-acetonitrile; {5-[(Methyl-phenethyl-amino)-methyl]-4-trifluoromethyl-thiazol-2-yl}-(2,4,6-trichloro-phenyl)-amine; (5-{[(2,2,3,3,3-Pentafluoro-propyl)-propyl-amino]-methyl}-4-trifluoromethyl-thiazol-2-yl)-(2,4,6-trichloro-phenyl)-amine; (5-{[Bis-(2-methyl-allyl)-amino]-methyl}-4-trifluoromethyl-thiazol-2-yl)-(2,4,6-trichloro-phenyl)-amine; {5-[(Furan-2-ylmethyl-propyl-amino)-methyl]-4-trifluoromethyl-thiazol-2-yl}-(2,4,6-trichloro-phenyl)-amine; (5-{[(2-Cyclopropyl-ethyl)-(3,3,3-trifluoro-propyl)-amino]-methyl}-4-trifluoromethyl-thiazol-2-yl)-(2,4,6-trichloro-phenyl)-amine; {5-[(Isobutyl-methyl-amino)-methyl]-4-trifluoromethyl-thiazol-2-yl}-(2,4,6-trichloro-phenyl)-amine; {5-[(Isobutyl-methyl-amino)-methyl]-4-trifluoromethyl-thiazol-2-yl}-(2,4,6-trichloro-phenyl)-amine; (5-{[(2-Cyclopropyl-ethyl)-ethyl-amino]-methyl}-4-trifluoromethyl-thiazol-2-yl)-(2,4,6-trichloro-phenyl)-amine; (5-Methylsulfanyl-[1,3,4]thiadiazol-2-yl)-[2-(2,4,6-trichloro-phenylamino)-4-trifluoromethyl-thiazol-5-ylmethyl]-amine; {5-[(Ethyl-methyl-amino)-methyl]-4-trifluoromethyl-thiazol-2-yl}-(2,4,6-trichloro-phenyl)-amine; [5-(2-Ethyl-imidazol-1-ylmethyl)-4-trifluoromethyl-thiazol-2-yl]-(2,4,6-trichloro-phenyl)-amine; (5-{[2-(3,4-Dichloro-phenyl)-ethylamino]-methyl}-4-trifluoromethyl-thiazol-2-yl)-(2,4,6-trichloro-phenyl)-amine; {5-[(Butyl-methyl-amino)-methyl]-4-trifluoromethyl-thiazol-2-yl}-(2,4,6-trichloro-phenyl)-amine; (2,4,6-Trichloro-phenyl)-(4-trifluoromethyl-5-{[2-(3-trifluoromethyl-phenyl)-ethylamino]-methyl}-thiazol-2-yl)-amine; {5-[(4-Chloro-benzylamino)-methyl]-4-trifluoromethyl-thiazol-2-yl}-(2,4,6-trichloro-phenyl)-amine; (5-{[Bis-(2-methoxy-ethyl)-amino]-methyl}-4-trifluoromethyl-thiazol-2-yl)-(2,4,6-trichloro-phenyl)-amine; {5-[(Methyl-pentyl-amino)-methyl]-4-trifluoromethyl-thiazol-2-yl}-(2,4,6-trichloro-phenyl)-amine; {5-[(3,4-Dichloro-benzylamino)-methyl]-4-trifluoromethyl-thiazol-2-yl}-(2,4,6-trichloro-phenyl)-amine; [5-(2-Methoxymethyl-pyrrolidin-1-ylmethyl)-4-trifluoromethyl-thiazol-2-yl]-(2,4,6-trichloro-phenyl)- amine; (5-{[2-(4-Chloro-phenyl)-ethylamino]-methyl}-4-trifluoromethyl-thiazol-2-yl)-(2,4,6-trichloro-phenyl)-amine; {5-[(Cyclohexylmethyl-propyl-amino)-methyl]-4-trifluoromethyl-thiazol-2-yl}-(2,4,6-trichloro-phenyl)-amine; [5-(2,5-Dihydro-pyrrol-1-ylmethyl)-4-trifluoromethyl-thiazol-2-yl]-(2,4,6-trichloro-phenyl)-amine; (5-{[2-(3-Fluoro-phenyl)-ethylamino]-methyl}-4-trifluoromethyl-thiazol-2-yl)-(2,4,6-trichloro-phenyl)-amine; (5-{[(4-Fluorobenzyl)-propyl-amino]-methyl}-4-trifluoromethylthiazol-2-yl)-(2,4,6-trichlorophenyl)-amine; (5-{[(3-Fluorobenzyl)-propyl-amino]-methyl}-4-trifluoromethylthiazol-2-yl)-(2,4,6-trichlorophenyl)-amine; {5-[(Propyl-pyridin-3-ylmethyl-amino)-methyl]-4-trifluoromethylthiazol-2-yl}-(2,4,6-trichloro-phenyl)-amine; {5-[(Propyl-pyridin-2-ylmethyl-amino)-methyl]-4-trifluoromethylthiazol-2-yl}-(2,4,6-trichlorophenyl)-amine; {5-[(Propyl-pyridin-4-ylmethyl-amino)-methyl]-4-trifluoromethylthiazol-2-yl}-(2,4,6-trichlorophenyl)-amine; {5-[(Phenethyl-propyl-amino)-methyl]-4-trifluoromethylthiazol-2-yl}-(2,4,6-trichlorophenyl)-amine; {5-[(Phenethyl-ethyl-amino)-methyl]-4-trifluoromethylthiazol-2-yl}-(2,4,6-trichlorophenyl)-amine; {5-[(Allyl-propyl-amino)-methyl]-4-trifluoromethylthiazol-2-yl}-(2,4,6-trichlorophenyl)-amine; (5-{[(4-Fluorobenzyl)-(2,2,2-trifluoroethyl)-amino]-methyl}-4-trifluoromethylthiazol-2-yl)-(2,4,6-trichlorophenyl)-amine; (5-{[(4-Chlorobenzyl)-(2,2,2-trifluoroethyl)-amino]-methyl}-4-trifluoromethylthiazol-2-yl)-(2,4,6-trichlorophenyl)-amine; (5-{[(3-Fluorobenzyl)-(2,2,2-trifluoroethyl)-amino]-methyl}-4-trifluoromethylthiazol-2-yl)-(2,4,6-trichlorophenyl)-amine; (5-{[(4-Fluorobenzyl)-(3,3,3-trifluoropropyl)-amino]-methyl}-4-trifluoromethylthiazol-2-yl)-(2,4,6-trichlorophenyl)-amine; (5-{[(4-Chlorobenzyl)-(3,3,3-trifluoropropyl)-amino]-methyl}-4-trifluoromethylthiazol-2-yl)-(2,4,6-trichlorophenyl)-amine; (5-{[(3-Fluorobenzyl)-(3,3,3-trifluoropropyl)-amino]-methyl}-4-trifluoromethylthiazol-2-yl)-(2,4,6-trichlorophenyl)-amine; (2-Chloro-4,6-dimethyl-phenyl)-{5-[(cyclopropylmethyl-propyl-amino)-methyl]-4-trifluoromethylthiazol-2-yl}-methyl-amine; (2-Chloro-4,6-dimethyl-phenyl)-{5-[(cyclopropylmethyl-propyl-amino)-methyl]-4-trifluoromethylthiazol-2-yl}-ethyl-amine; and (2-Bromo-4-isopropyl-phenyl)-{5-[(cyclopropylmethyl-propyl-amino)-methyl]-4-trifluoromethylthiazol-2-yl}-ethyl-amine.

According to another embodiment of the first aspect of the present invention are compounds of Formula (I) as defined herein having $IC_{50}$ values of 10 nM or less as described herein.

According to another embodiment of the first aspect of the present invention are compounds of Formula (I) as defined herein having $IC_{50}$ values greater than 10 nM but less than 50 nM as described herein.

According to another embodiment of the first aspect of the present invention are compounds of Formula (I) as defined herein having $IC_{50}$ values greater than 50 nM but less than 100 nM as described herein.

According to another embodiment of the first aspect of the present invention are compounds of Formula (I) as defined herein having $IC_{50}$ values greater than 100 nM but less than 1000 nM as described herein.

According to another embodiment of the first aspect of the present invention are compounds of Formula (I) as defined herein having $IC_{50}$ values greater than 1,000 nM but less than 10,000 nM as described herein.

According to various embodiments of a second aspect of the present invention are provided pharmaceutical compositions comprising compounds of Formula (I) as defined herein.

According to various embodiments of a third aspect of the present invention are provided methods of treating depression, anxiety, affective disorders, feeding disorders, post-traumatic stress disorder, headache, drug addiction, inflammatory disorders, drug or alcohol withdrawal symptoms and other conditions the treatment of which can be effected by the antagonism of the CRF-1 receptor by the administration of an effective amount of a pharmaceutical composition comprising a compound according to claim 1 to a human in need thereof.

Other embodiments of the present invention may comprise a suitable combination of two or more of embodiments and/or aspects disclosed herein.

Yet other embodiments and aspects of the invention will be apparent according to the description provided below.

DETAILED DESCRIPTION OF THE INVENTION

The description of the invention herein should be construed in congruity with the laws and principals of chemical bonding. Alkyl groups as described herein may be straight or branched. Non-limiting examples of $C_{1-6}$alkyl groups include as methyl, ethyl, n-propyl, isopropyl, n-butyl, sec-butyl, isobutyl, t-butyl, n-pentyl, sec-pentyl, isopentyl and n-hexyl. An embodiment or aspect which depends from another embodiment or aspect, will describe only the variables having values and provisos that differ from the embodiment or aspect from which it depends. The term "halo" or "halogen" includes fluoro, chloro, bromo and iodo. Where "halo" is used to describe another moiety, e.g., "haloalkyl", one or more of the same or different halogens may be substituted on said alkyl. It is to be understood that the present invention may include any and all possible stereoisomers, geometric isomers, diastereoisomers, enantiomers, anomers and optical isomers, unless a particular description specifies otherwise.

The compounds of this invention can exist in the form of pharmaceutically acceptable salts. Such salts include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group can exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

The dosage and dosage regimen and scheduling of a compounds of the present invention must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level which will produce effective beneficial effects without causing any harmful or untoward side effects.

Compounds of the present invention may be synthesized according to the general schema provided below. Variables provided in the schema below are defined in accordance with the description of compounds of Formula (I) unless otherwise specified.

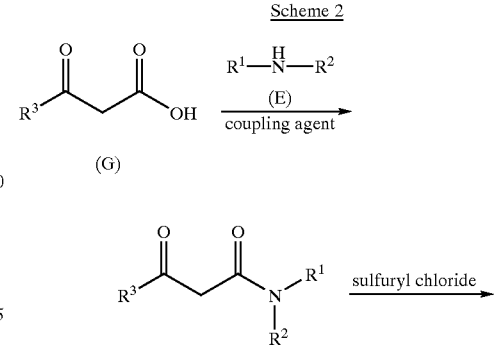

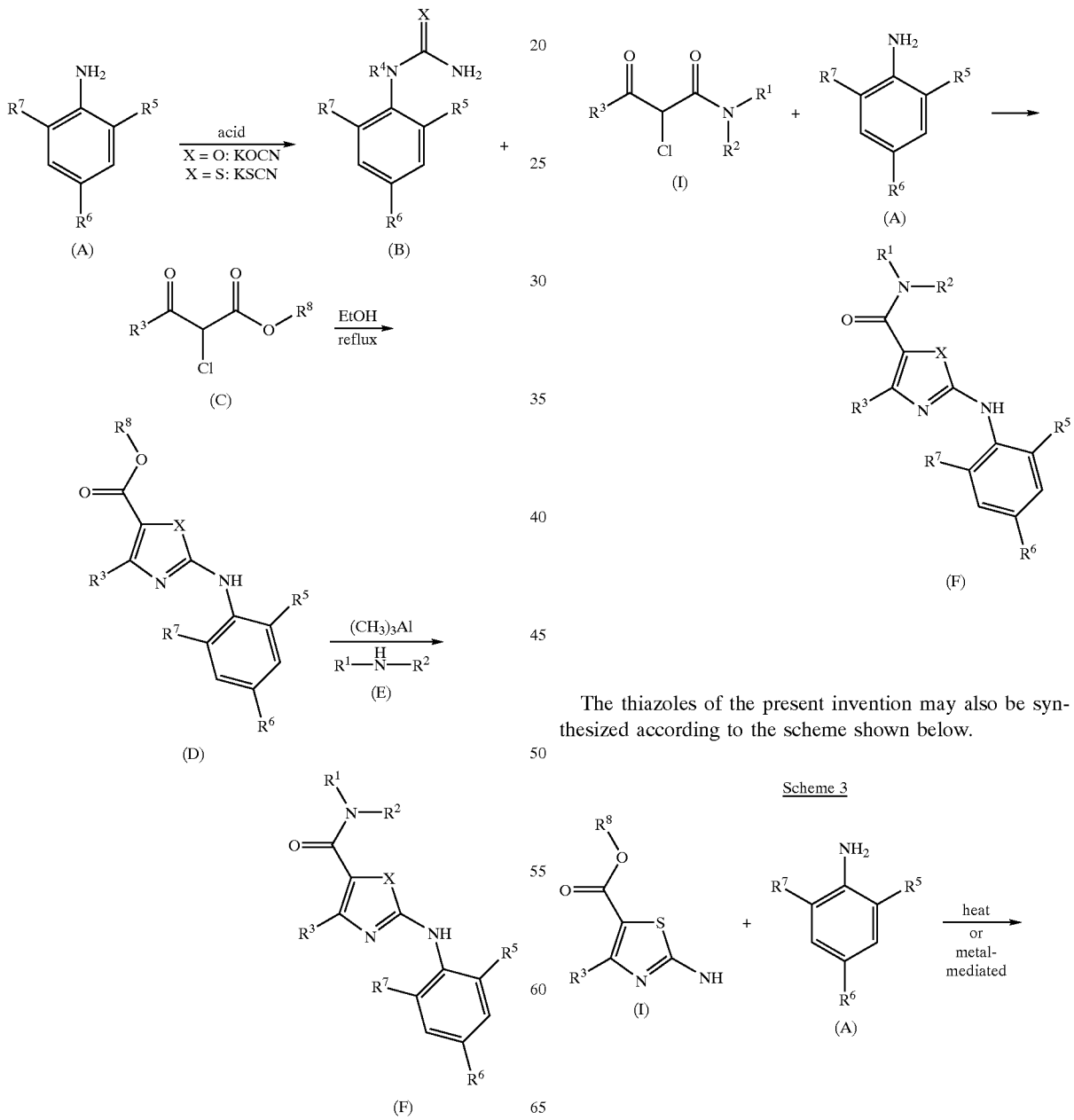

The thiazoles of the present invention may also be synthesized according to the scheme shown below.

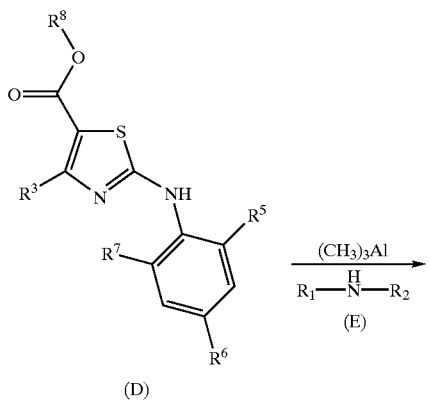
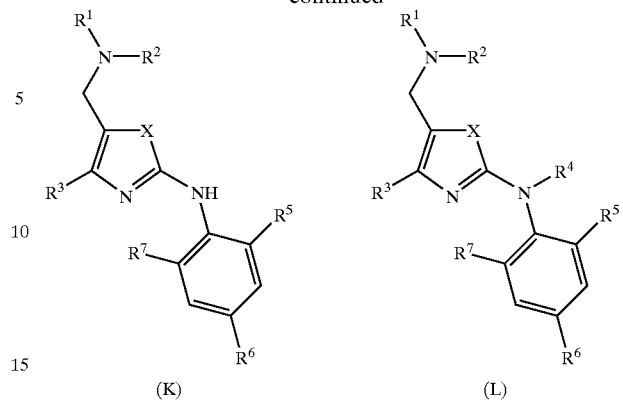
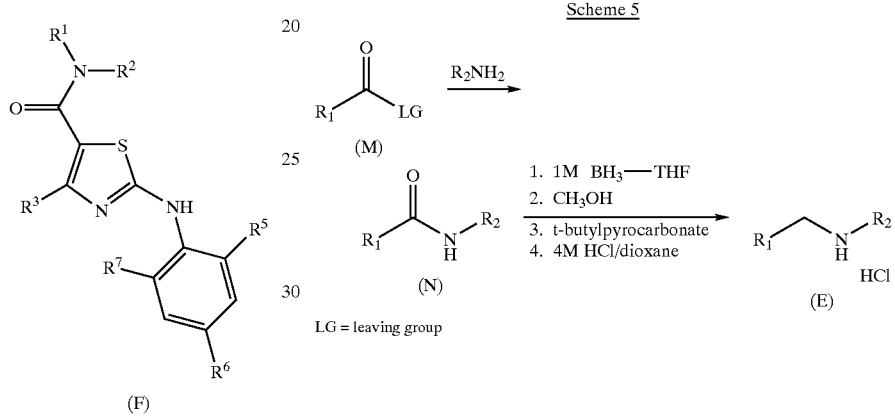
The compounds prepared as described above can be further modified as shown below.
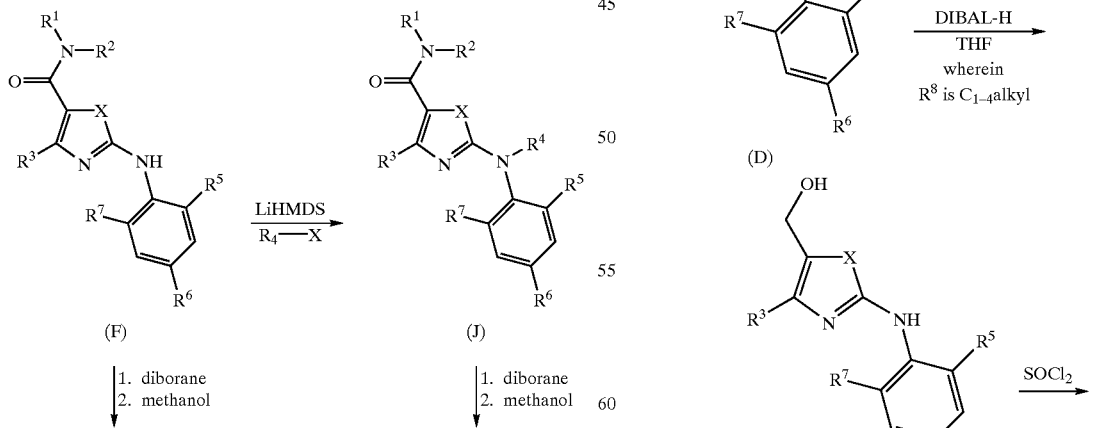
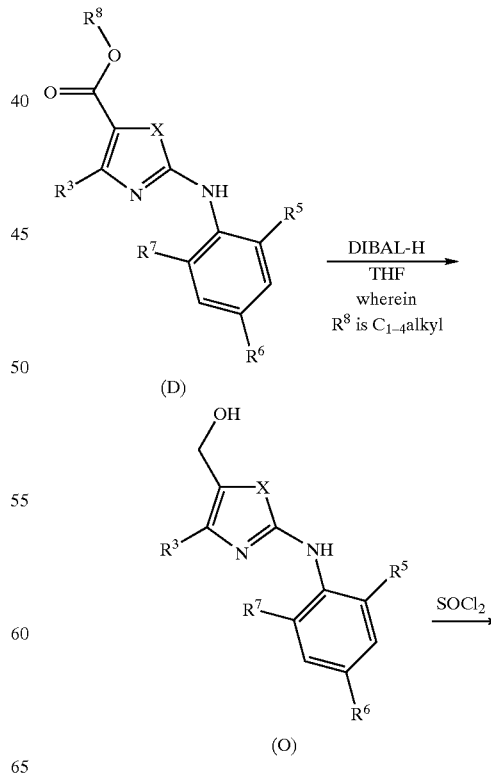

-continued

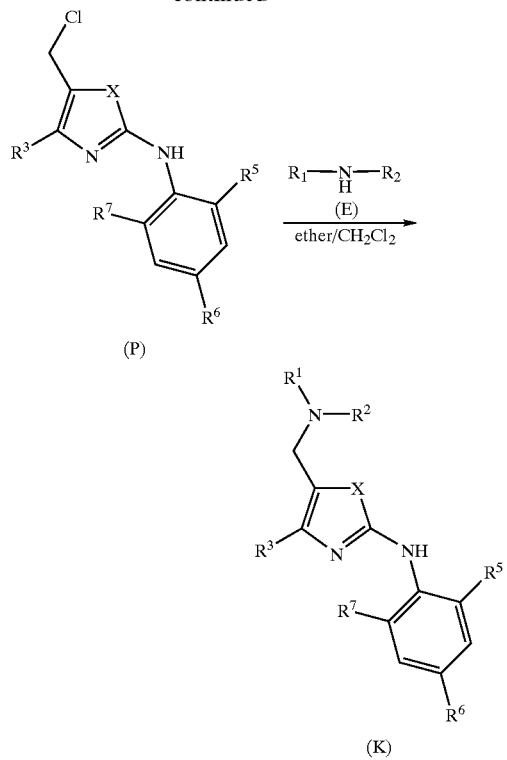

X = S, O, NR

Other suitable means of synthesizing said compounds may also be available. More detailed descriptions of synthesizing compounds of the present invention are also provided.

PREPARATION OF INTERMEDIATES

First Set of Intermediates

Ethyl 2-Bromo-4-methylthiazole-5-carboxylate, Scheme 3: (I)

Ethyl 2-amino-4-methylthiazole-5-carboxylate (1.20 g, 6.44 mmoles) was added to a solution of 85% phosphoric acid (18 mL) and 70% nitric acid (9 mL) at 0° C. Aqueous sodium nitrite(1.38 g (20 mmol) in water (9 mL) was immediately added dropwise over 20 minutes. After stirring at 0° C. for 15 minutes, cuprous bromide (930 mg, 6.44 mmoles) in hydrobromic acid (9 mL) was added. After stirring for 10 minutes, water (30 mL) was added. The mixture was filtered and the crude solid purified via silica gel chromatography (10% ethyl acetate/hexane) to afford 1.15 g (4.6 mmoles) of the product as a yellow solid (71%). $H^1$ NMR (CDCl$_3$) δ 4.35 (2H, q, J=7.1 Hz), 2.73 (3H, s), 1.38 (3H, t, J=7.1 Hz).

Ethyl 2-(2,4,6-Trichlorophenylamino)-4-methylthiazole-5-carboxylate, Scheme 3: (D)

Sodium Hydride (920 mg, 13.8 mmoles) was added to a solution of 2,4,6-trichloroaniline (scheme 3: (A)) (1.17g, 5.9 mmoles) in tetrahydrofuran (5 mL). After 10 minutes, the mixture was added to a solution of ethyl 2-bromo-4-methylthiazole-5-carboxylate (scheme 3: (I)) (1.15 g, 4.6 mmoles) in tetrahydrofuran (5 mL). The reaction was stirred at room temperature for one hour, and then at 70° C. for a further hour. TLC (30% ethyl acetate/hexane) indicated consumption of starting material. Water was added and the aqueous layer extracted with ethyl acetate (3x). The combined organic phases were dried over MgSO$_4$, and concentrated in vacuo. The crude solid was purified via silica gel chromatography to afford 1.09 g (65%) as a yellow solid. $H^1$ NMR (CDCl$_3$) δ 7.46 (2H, s), 4.22 (2H, q, J=7.1 Hz), 2.50 (3H, s), 1.28 (3H, t, J=7.1 Hz).

Ethyl 2-(2-Bromo-4-isopropylphenylamino)-4-methylthiazole-5-carboxylate, Scheme 3: (D)

A solution of ethyl 2-bromo-4-methylthiazole-5-carboxylate (scheme 3: (I)) (138 mg, 0.55 mmoles) and 2-bromo-4-isopropyl aniline (scheme 3: (A)) (118 mg, 0.55 mmoles) in dioxane (3 mL) was heated at reflux for 14 hours. The solution was concentrated in vacuo and purified via silica gel chromatography to afford 150 mg (71%) as a yellow solid. $H^1$ NMR (CDCl$_3$) δ 7.73–7.71 (1H, d), 7.48 (1H, s), 7.28–7.22 (1H, m), 4.28 (2H, q, J=7.1 Hz), 2.94–2.85 (1H, m), 2.59 (3H, s), 1.36 (3H, t, J=7.1 Hz), 1.27 (3H, s), 1.25 (3H, s).

Methyl 2-(2,4,6-Trichlorophenylamino)-4-ethylthiazole-5-carboxylate, Scheme 1: (D)

A stirred solution of 2,4,6-trichlorophenylthiourea (scheme 1: (B)) (3.25 g, 12.72 mmoles) and methyl 2-chloro-3-oxopentanoate (Scheme 1: (C)) (1.92 mL, 1.1 equiv.) in ethanol (60 mL) was heated at reflux for 16 hours. The solvent was removed in vacuo and the product was recrystallized from methanol (4.49 g, 97%). $H^1$ NMR (CDCl$_3$) δ 1.15 (3H, t), 2.91 (2H, q), 3.75 (3H, s), 7.47 (2H, s), 9.10 (1H, br).

Ethyl 2-(2,4,6-Trichlorophenylamino)-4-trifluoromethylthiazole-5-carboxylate, Scheme 1: (D)

Prepared as described for the example above. $H^1$ NMR (CDCl$_3$) δ 1.31 (3H, t), 4.28 (2H, q), 7.51 (2H, s), 8.87 (1H, brs).

N-Cyclopropylmethyl-N-propyl-3-oxo-butanamide, Scheme 2: (H)

A stirred mixture of lithium acetoacetate (scheme 2: (G)) (1.00 g, 9.26 mmoles), triethylamine (2.58 mL, 18.5 mmoles), and n-propylcyclopropylmethyl amine (scheme 2: (E)) (1.32 mL, 9.26 mmoles) in dry dichloroethane (60 mL) was treated with bis(2-oxo-3-oxazolidinyl)phosphinic chloride (BOPCl) (2.36g, 9.26 mmoles). The mixture was stirred overnight at room temperature, and then acidified (pH~1) with 1M hydrochloric acid. The mixture was extracted with ethyl acetate, washed with saturated sodium bicarbonate, brine, and dried over MgSO$_4$. Concentration in vacuo and purification by silica gel chromatography (30% ethyl acetate/hexane) gave 900 mg of a yellow oil.

2-Chloro-N-cyclopropylmethyl-N-propyl-3-oxo-butanamide, Scheme 2: (I)

A stirred solution of N-cyclopropylmethyl-N-propyl-3-oxo-butanamide (scheme 2: (H)) (900 mg, 4.57 mmoles) in chloroform (30 mL) at 0° C. was treated with sulfuryl chloride (1M in methylene chloride, 5.48 mL, 5.48 mmoles). The mixture was stirred at room temperature for 30 minutes and then poured into methylene chloride and washed with 5% sodium bicarbonate solution, brine, and dried over Na$_2$SO$_4$. The solution was concentrated in vacuo and the crude product used without further purification.

N-(2,4,6-Trimethylphenyl)urea, Scheme 1: (B)

A vigorously stirred solution of 2,4,6-trimethylaniline (scheme 1: (A)) (15 mL, 0.107 moles) in acetic acid (60 mL) was treated with potassium cyanate (17.33 g, 2 equiv.). A heavy white precipitate soon formed. After 16 hours at room temperature, the mixture was poured into water. The product was collected by filtration, washed with water, and dried in vacuo overnight (19.05 g, 100%). $^1$H-NMR (DMSO-d$_6$) □ 2.22 (6H, s), 2.28 (3H, s), 5.73 (2H, br s), 6.92 (2H, s), 7.58 (1H, br). Mass spec.: 179.12 (MH$^+$).

N-(2-Chloro-4,6-dimethylphenyl)urea, Scheme 1: (B)

Prepared as described for the example above. $^1$H-NMR (DMSO-d$_6$) δ 2.16 and 2.24 (each 3H, s), 5.82 (2H, br s), 6.99 and 7.11 (each 1H, s), 7.65 (1H, br s). Mass spec.: 199.03 (MH$^+$).

2-(2,4,6-Trimethylphenylamino)-5-ethoxycarbonyl-4-methyloxazole, Scheme 1: (D)

A suspension of N-(2,4,6-trimethylphenyl)urea (scheme 1: (B)) (5.91 g, 33.16 mmoles) and ethyl 2-chloroacetoacetate (scheme 1: (C)) (4.6 mL, 1 equiv.) in ethanol (100 mL) was heated at reflux for 5 days. The mixture was cooled to room temperature and filtered. The filtrate was evaporated and the residue partitioned between saturated sodium bicarbonate and ether. The ether phase was washed with water and brine, dried over magnesium sulfate, and evaporated. The residue was purified by silica gel chromatography, eluting with 100:1 methylene chloride methanol, to give the product as a pale-yellow solid (2.48 g, 26%). $^1$H-NMR (CDCl$_3$) □ 1.36 (3H, t), 2.22 (6H, s), 2.27 (3H, s), 2.34 (3H, s), 4.32 (2H, q), 6.46 (1H, br), 6.92 (2H, s). Mass spec.: 289.16 (MH$^+$).

2-(2-Chloro-4,6-dimethylphenylamino)-5-ethoxycarbonyl-4-methyloxazole, Scheme 1: (D)

Prepared as described for the example above. $^1$H-NMR (CDCl$_3$) □ 1.31 (3H, t), 2.26, 2.28 and 2.30 (each 3H, s), 4.27 (2H, q), 6.97 and 7.10 (each 1H, s), 7.82 (1H, br). Mass spec.: 309.07 (MH$^+$).

Second Set of Intermediates

The following Intermediates 1–2 of the Second Set of Intermediates may be used to synthesize Examples 1–63 of the Second Set of Examples.

Intermediate 1

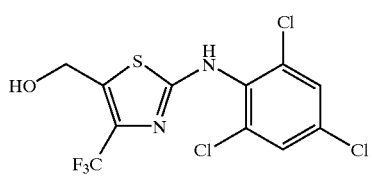

[2-(2,4,6-Trichloro-phenylamino)-4-trifluoromethyl-thiazol-5-yl]-methanol, Scheme 6: (O)

To a solution of ethyl ester (1.000 g, 2.383 mmol) in THF (50 mL) at 0° C. was added a 1.0M solution of DIBAL-H in THF (12.0 mL, 12.000 mmol) over a 30 minute period. The resulting solution was warmed to room temperature and stirred for 2 h. Acetone (5 mL) was added and the solution was cannulated into a vigorously stirred ice-cold solution of Rochelle's salt (200 mL). The product was extracted with ethyl acetate (5×50 mL) and the combined organic extracts were dried over anhydrous Na$_2$SO$_4$. The solvent was removed in vacuo and the crude product (0.897 g, 100%) which was pure by LC-MS and $^1$H NMR, and was used in the next step without further purification. $^1$H NMR (DMSO D6, 500 MHz) δ 10.00 (s, 1H), 7.82 (s, 2H), 5.84 (t, J=5.6 Hz, 1H), 4.63 (s, 2H); Mass spec: 376.87 (MH$^+$).

Intermediate 2

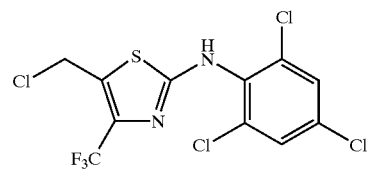

(5-Chloromethyl-4-trifluoromethyl-thiazol-2-yl)-(2,4,6-trichloro-phenyl)-amine, Scheme 6: (P)

A solution of alcohol (436.3 mg, 1.155 mmol) in thionyl chloride (7.0 mL) was heated at 85° C. for 5 min. The resulting solution was cooled down to room temperature. Thionyl chloride was removed in vacuo and the residue was dried on the pump to yield the desired product as a yellow solid (388.8 mg, 85%). The purity of the product determined by LCMS was 91%. $^1$H-NMR (CDCl$_3$) δ 4.68 (s, 2H), 7.49 (s, 2H), 8.82 (br, 1H).

Intermediate 3

2-Cyclopropylethylamine Hydrochloride, Scheme 5: (E)

A 1M solution of borane in tetrahydrofuran (250 mL, 2 equiv.) that had been cooled to 0° C. was added to cyclopropylacetonitrile (10.00 g, 123.3 mmoles) at 0° C. under nitrogen. The stirred mixture was heated at reflux for 12 hours, cooled to 0° C., and then carefully quenched with methanol (50 mL). The mixture was heated at reflux for 2 hours and then, upon re-cooling to 0° C., treated with a solution of t-butylpyrocarbonate (37.67 g, 1.4 equiv.) in methylene chloride (25 mL). The resulting mixture was stirred at room temperature overnight and then evaporated. The residue was partitioned between ethyl acetate and water. The organic was washed with water, brine, dried over magnesium sulfate, and evaporated to give the crude Boc-protected amine. This was dissolved in methylene chloride (25 mL) and treated with 4M hydrogen chloride in dioxane (77 mL, 2.5 equiv.). The mixture was stirred at room temperature overnight and then evaporated. The resulting white solid was triturated with ether and the product was collected by filtration, washed with ether, and dried in vacuo (12.72 g, 85%). $^1$H-NMR δ (CDCl$_3$) 0.14 (m, 2H), 0.52 (m, 2H), 0.75 (m, 1H), 1.66 (q, 2H), 3.09 (m, 2H), 8.27 (br, 3H).

Intermediate 4

3,3,3-Trifluoroacetic Acid N-hydroxysuccinimide Active Ester, Scheme 5: (M)

A stirred solution of 3,3,3-trifluoroacetic acid (9.7 mL, 110 mmoles) and N-hydroxysuccinimide (13.92 g, 1.1 equiv.) in methylene chloride (100 mL) at 0° C. was treated with EDC hydrochloride (21.08 g, 1 equiv.). The mixture was allowed to warm to room temperature. After stirring overnight, the solvent was evaporated and the residue partitioned between ethyl acetate and water. The organic phase was washed with brine, dried over magnesium sulfate, and evaporated to give the crude active ester which was used without further purification (22.78 g, 92%). $^1$H-NMR δ (CDCl$_3$) 2.86 (s, 4H), 3.51 (q, 2H).

Intermediate 5

Cyclopropylmethyl-3,3,3-trifluoropropyl-amine Hydrochloride, Scheme 5: (E)

A stirred solution of 3,3,3-trifluoroacetic acid N-hydroxysuccinimide active ester (12.98 g, 57.65 mmoles) in methylene chloride (80 mL) at 0° C. was treated with cyclopropylmethylamine (5.0 mL, 1 equiv.). The mixture was stirred at room temperature for 14 hours and then evaporated. The residue was partitioned between ethyl acetate and water. The organic phase was washed with water, brine, dried over magnesium sulfate, and evaporated to give the crude amide. This was dried under high vacuum for several hours and then, under a nitrogen atmosphere at 0° C., it was carefully treated with a 1M solution of borane in tetrahydrofuran (173 mL, 3 equiv.). The mixture was heated at reflux for 14 hours and then re-cooled to 0° C. Methanol (50 mL) was added very carefully to avoid excess foaming, and the mixture was heated at reflux for 5 hours. Upon re-cooling to 0° C., a solution of t-butylpyrocarbonate (17.62 g, 1.4 equiv.) in methylene chloride (25 mL) was added. The resulting mixture was stirred at room temperature overnight and then evaporated. The residue was partitioned between ethyl acetate and water. The organic was washed with water, brine, dried over magnesium sulfate, and evaporated to give the crude Boc-protected amine. This was dissolved in methylene chloride (25 mL) and treated with 4M hydrogen chloride in dioxane (36 mL, 2.5 equiv.). The mixture was stirred at room temperature overnight and then evaporated. The resulting white solid was triturated with ether and the product was collected by filtration, washed with ether, and dried in vacuo (10.10 g, 86%). $^1$H-NMR δ (D$_2$O) 0.36 (m, 2H), 0.67 (m, 2H), 1.07 (m, 1H), 2.72 (m, 2H), 2.99 (d, 2H), 3.89 (t, 2H).

Similarly prepared:

Intermediate 6

2-Cyclopropylethyl-3,3,3-trifluoropropyl-amine Hydrochloride, Scheme 5: (E)

$^1$H-NMR δ (D$_2$O) 0.14 (m, 2H), 0.52 (m, 2H), 0.74 (m, 1H), 1.61 (m, 2H), 2.73 (m, 2H), 3.20 (t, 2H), 3.38 (t, 2H).

Intermediate 7 n-Propyl-3,3,3-trifluoropropyl-amine Hydrochloride, Scheme 5: (E)

$^1$H-NMR δ (D$_2$O) 0.98 (t, 3H), 1.71 (q, 2H), 2.72 (m, 2H), 3.06 (t, 2H), 3.36 (t, 2H).

Intermediate 8

Benzyl-3,3,3-trifluoropropyl-amine Hydrochloride, Scheme 5: (E)

$^1$H-NMR δ (D$_2$O) 2.73 (m, 2H), 3.40 (t, 2H), 4.31 (s, 2H), 7.51 (brs, 5H).

Intermediate 9 p-Fluoro-benzyl-3,3,3-trifluoropropyl-amine Hydrochloride, Scheme 5: (E)

$^1$H-NMR δ (D$_2$O) 2.73 (m, 2H), 3.38 (t, 2H), 4.28 (s, 2H), 7.23 (ABq, 2H), 7.51 (ABq, 2H).

Intermediate 10 p-Chloro-benzyl-3,3,3-trifluoropropyl-amine Hydrochloride, Scheme 5: (E)

$^1$H-NMR δ (D$_2$O) 2.72 (m, 2H), 3.39 (t, 2H), 4.29 (s, 2H), 7.49 (q, 4H).

Intermediate 11 m-Fluoro-benzyl-3,3,3-trifluoropropyl-amine Hydrochloride, Scheme 5: (E)

$^1$H-NMR δ (D$_2$O) 2.73 (m, 2H), 3.41 (t, 2H), 4.39 (s, 2H), 7.30 (m, 3H), 7.66 (m, 1H).

Intermediate 12

2-Phenylethyl-3,3,3-trifluoropropyl-amine Hydrochloride, Scheme 5: (E)

$^1$H-NMR δ (D$_2$O) 2.73 (m, 2H), 3.07 (t, 2H), 3.40 (m, 4H), 7.42 (m, 5H).

Intermediate 13

Benzyl-2,2,2-trifluoroethyl-amine Hydrochloride, Scheme 5: (E)

A stirred solution of benzylamine (5.0 mL, 45.77 mmoles) and triethylamine (6.4 mL, 1 equiv.) in methylene chloride (50 mL) at 0° C. was treated with trifluoroacetic anhydride (6.5 mL, 1 equiv.), dropwise over 10 minutes. After 2 hours, the solvents were evaporated and the residue partitioned between ethyl acetate and 2% phosphoric acid. The organic phase was washed with water and brine, dried over magnesium sulfate, and evaporated. The crude amide was cooled to 0° C. under nitrogen and treated with ice-cold 1M borane-tetrahydrofuran complex (137 mL, 3 equiv.). The reaction mixture was heated at reflux for 14 hours and then cooled to 0° C. Methanol (50 mL) was carefully added and, when bubbling had largely ceased, the mixture was heated at reflux for 5 hours. Upon cooling to room temperature, the stirred mixture was treated with a solution of t-butylpyrocarbonate (14.00 g, 1.4 equiv.) in methylene chloride (25 mL). After continued stirring overnight at room temperature, the mixture was evaporated and the residue partitioned between ethyl acetate and water. The organic phase was washed with more water and brine, dried over magnesium sulfate, and evaporated. The residue in methylene chloride (25 mL) was treated with 4M hydrogen chloride in dioxane (69 mL, 1.5 equiv.) and the reaction was stirred at room temperature overnight. Evaporation gave a semi-solid that was triturated with ether. The resulting white solid product was collected by filtration, washed with ether, and dried in vacuo (9.28 g, 90%). $^1$H-NMR δ (D$_2$O) 3.97 (q, 2H), 4.07 (s, 2H), 7.52 (s, 5H).

Similarly prepared:

Intermediate 14

Cyclopropylmethyl-2,2,2-trifluoroethyl-amine Hydrochloride, Scheme 5: (E)

$^1$H-NMR δ (D$_2$O) 0.39 (m, 2H), 0.72 (q, 2H), 1.08 (m, 1H), 3.11 (d, 2H), 4.00 (q, 2H).

Intermediate 15

Cyclobutylmethyl-2,2,2-trifluoroethyl-amine Hydrochloride, Scheme 5: (E)

$^1$H-NMR δ (D$_2$O) 1.75–2.02 (m, 4H), 2.12 (m, 2H), 2.71 (m, 1H), 3.24 (d, 2H), 3.93 (q, 2H).

Intermediate 16

2-Cyclopropylethyl-2,2,2-trifluoroethyl-amine Hydrochloride, Scheme 5: (E)

$^1$H-NMR δ (D$_2$O) 0.14 (m, 2H), 0.53 (m, 2H), 0.76 (m, 1H), 1.64 (q, 2H), 3.30 (t, 2H), 3.98 (q, 2H).

Intermediate 17 n-Propyl-2,2,2-trifluoroethyl-amine Hydrochloride, Scheme 5: (E)

$^1$H-NMR δ (D$_2$O) 1.00 (t, 3H), 1.76 (m, 2H), 3.17 (t, 2H), 3.97 (q, 2H).

Intermediate 18 p-Fluorobenzyl-2,2,2-trifluoroethyl-amine Hydrochloride, Scheme 5: (E)

$^1$H-NMR δ (D$_2$O) 3.98 (q, 2H), 4.40 (s, 2H), 7.24 (t, 2H), 7.53 (m, 2H).

Intermediate 19 m-Fluorobenzyl-2,2,2-trifluoroethyl-amine Hydrochloride, Scheme 5: (E)

$^1$H-NMR δ (D$_2$O) 3.97 (q, 2H), 4.39 (s, 2H), 7.30 (m, 3H), 7.66 (m, 1H).

Intermediate 20 p-Chlorobenzyl-2,2,2-trifluoroethyl-amine Hydrochloride, Scheme 5: (E)

$^1$H-NMR δ (D$_2$O) 3.98 (q, 2H), 4.39 (s, 2H), 7.50 (m, 4H).

Intermediate 21

2-Phenylethyl-2,2,2-trifluoroethyl-amine Hydrochloride, Scheme 5: (E)

$^1$H-NMR δ (D$_2$O) 3.10 (t, 2H), 3.49 (t, 2H), 4.00 (q, 2H), 7.41 (m, 5H).

Intermediate 22

Cyclopropylmethyl-2,2,3,3,3-pentafluoropropyl-amine Hydrochloride, Scheme 5: (E)

$^1$H-NMR δ (D$_2$O) 0.41 (m, 2H), 0.72 (m, 2H), 1.21 (m, 1H), 3.14 (d, 2H), 4.06 (t, 2H).

Intermediate 23 n-Propyl-2,2,3,3,3-pentafluoropropyl-amine Hydrochloride, Scheme 5: (E)

$^1$H-NMR δ (D$_2$O) 1.00 (t, 3H), 1.78 (m, 2H), 3.20 (t, 2H), 4.05 (t, 2H).

Intermediate 24 bis-Cyclopropylmethyl-amine Hydrochloride, Scheme 5: (E)

$^1$H-NMR δ (D$_2$O) 0.35 (m, 2H), 0.68 (m, 2H), 1.07 (m, 1H), 2.95 (d, 2H).

Intermediate 25

Cyclopropylmethyl-ethyl-amine Hydrochloride, Scheme 5: (E)

$^1$H-NMR δ (D$_2$O) 0.34 (m, 2H), 0.67 (m, 2H), 1.04 (m, 1H), 1.27 (t, 3H), 2.90 (d, 2H), 3.08 (q, 2H).

Intermediate 26

2-Cyclopropylethyl-ethyl-amine Hydrochloride, Scheme 5: (E)

$^1$H-NMR δ (D$_2$O) 0.12 (m, 2H), 0.51 (m, 2H), 0.73 (m, 1H), 1.28 (t, 3H), 1.60 (m, 2H), 3.12 (m, 4H).

Intermediate 27

2-Cyclopropylethyl-propyl-amine hydrochloride, Scheme 5: (E)

$^1$H-NMR δ (D$_2$O) 0.13 (m, 2H), 0.51 (m, 2H), 0.72 (m, 1H), 0.97 (t, 3H), 1.58 (q, 2H), 1.66 (m, 2H), 3.00 (t, 2H), 3.13 (t, 2H).

Intermediate 28

Cyclobutylmethyl-propyl-amine Hydrochloride, Scheme 5: (E)

$^1$H-NMR δ (D$_2$O) 0.95 (t, 3H), 1.60–2.05 (m, 6H), 2.10 (m, 2H), 2.62 (m, 1H), 2.96 (t, 2H), 3.06 (t, 2H).

Intermediate 29

Benzyl-propyl-amine Hydrochloride, Scheme 5: (E)

$^1$H-NMR δ (D$_2$O) 0.96 (t, 3H), 1.71 (m, 2H), 3.04 (t, 2H), 4.23 (s, 2H), 7.50 (m, 5H).

Intermediate 30

3-Pyridylmethyl-propyl-amine Hydrochloride, Scheme 5: (E)

$^1$H-NMR δ (D$_2$O) 0.99 (t, 3H), 1.73 (m, 2H), 3.13 (t, 2H), 4.51 (s, 2H), 8.11 (t, 1H), 8.67 (d, 1H), 8.87 (d, 1H), 8.95 (s, 1H).

Intermediate 31

2-Pyridylmethyl-propyl-amine Hydrochloride, Scheme 5: (E)

$^1$H-NMR δ (D$_2$O) 0.97 (t, 3H), 1.71 (m, 2H), 3.14 (t, 2H), 4.50 (s, 2H), 7.81 (m, 2H), 8.30 (m, 1H), 8.56 (d, 1H).

Intermediate 32

4-Pyridylmethyl-propyl-amine Hydrochloride, Scheme 5: (E)

$^1$H-NMR δ (D$_2$O) 1.00 (t, 3H), 1.77 (m, 2H), 3.21 (t, 2H), 4.61 (s, 2H), 8.18 (d, 2H), 8.91 (d, 2H).

Intermediate 33 p-Fluorobenzyl-propyl-amine Hydrochloride, Scheme 5: (E)

$^1$H-NMR δ (D$_2$O) 0.96 (t, 3H), 1.73 (m, 2H), 3.03 (t, 2H), 4.22 (s, 2H), 7.22 (t, 2H), 7.51 (m, 2H).

Intermediate 34 m-Fluorobenzyl-propyl-amine Hydrochloride, Scheme 5: (E)

$^1$H-NMR δ (D$_2$O) 0.98 (t, 3H), 1.73 (m, 2H), 3.14 (t, 2H), 4.39 (s, 2H), 7.30 (m, 3H), 7.65 (m, 1H).

Intermediate 35 p-Chlorobenzyl-propyl-amine Hydrochloride, Scheme 5: (E)

$^1$H-NMR δ (D$_2$O) 0.96 (t, 3H), 1.71 (m, 2H), 3.03 (t, 2H), 4.22 (s, 2H), 7.47 (q, 4H).

Intermediate 36

2-Phenylethyl-propyl-amine Hydrochloride, Scheme 5: (E)

$^1$H-NMR δ (D$_2$O) 0.95 (t, 3H), 1.69 (m, 2H), 3.05 (m, 4H), 3.32 (t, 2H), 7.37 (m, 5H).

Intermediate 37

2-Phenylethyl-ethyl-amine Hydrochloride Scheme 5: (E)

$^1$H-NMR δ (D$_2$O) 1.26 (t, 3H), 3.11 (m, 4H), 3.32 (t, 2H), 7.41 (m, 5H).

Intermediate 38

Allyl-propylamine Hydrochloride, Scheme 5: (E)

A stirred solution of allylamine (10.0 mL, 133.3 mmoles) in methylene chloride (80 mL) at 0° C. was treated with propionic anhydride (8.54 mL, 0.5 equiv.), dropwise over 10 minutes. After 2 hours, the solvents were evaporated and the residue partitioned between ethyl acetate and 2% phosphoric acid. The organic phase was washed with brine, dried over magnesium sulfate, and evaporated. The crude amide in toluene (10 mL) was cooled to 0° C. under nitrogen and treated with a 3.33M solution of Red-Al in toluene (7.1 mL, 2.5 equiv.). After stirring at room temperature for 14 hours, the mixture was cooled to 0° C. and carefully quenched with acetone (12 mL). The reaction was allowed to warm to room temperature and then was treated with methanol (3 mL) and, after a further 1 hour at room temperature, a solution of t-butylpyrocarbonate (2.87 g, 1.4 equiv.) in methylene chloride (5 mL). After 14 hours at room temperature, the solvents were evaporated and the residue partitioned between ethyl acetate and 10% aqueous citric acid. The organic phase was washed with more water and brine, dried over magnesium sulfate, and evaporated. The residue in methylene chloride (5 mL) was treated with 4M hydrogen chloride in dioxane (6 mL, 2.5 equiv.) and the reaction was stirred at room temperature overnight. Evaporation gave a semi-solid that was triturated with ether. The resulting white solid product was collected by filtration, washed with ether, and dried in vacuo (0.760 g, 60%). $^1$H-NMR δ (D$_2$O) 0.97 (t, 3H), 1.70 (m, 2H), 3.01 (t, 2H), 3.66 (d, 2H), 5.50 (t, 2H), 5.91 (m, 1H).

Preparation of Compounds of Formula (I)

FIRST SET OF EXAMPLES

Example 1

2-(2,4,6-Trichlorophenylamino)-5-(N-cyclopropylmethyl-N-n-propyl)aminocarbonyl-4-methylthiazole, Scheme 3: (F)

A solution of trimethyl aluminum (2M in toluene, 0.3 mL, 0.55 mmoles) was added to a stirred suspension of N-n-propyl-N-cyclopropylmethylamine hydrochloride (scheme 3: (E)) (0.55 mmoles) in benzene (1 mL) at 0° C. The mixture was warmed to room temperature and stirred for 1.5 hours, and then added to a stirred solution of ethyl 2-(2,4,6-trichlorophenylamino)-4-methylthiazole-5-carboxylate (scheme 3: (D)) (35.4 mg, 0.082 mmoles) in benzene (0.5 mL). The mixture was heated at reflux overnight. The solution was cooled to room temperature and quenched with 1M hydrochloric acid. The aqueous layer was extracted three times with ethyl acetate, and the combined organic solutions dried over MgSO$_4$, concentrated in vacuo and purified via silica gel chromatography (40% ethyl acetate/hexane) to afford 29 mg (82%) as a yellow solid. H$^1$ NMR (CDCl$_3$) δ 7.44 (2H, s), 3.50–3.45 (2H, m), 3.30 (2H, d, J=6.8 Hz), 2.22 (3H, s), 1.64–1.56 (2H, m), 1.30–1.25 (1H, m), 0.87 (3H, t, J=7.4 Hz), 0.57–0.50 (2H, m), 0.23–0.20 (2H, m).

Example 10

2-(2,4,6-Trichlorophenylamino)-5-(N-n-propyl-N-cyclopropylmethyl)aminocarbonyl-4-ethylthiazole, Scheme 1: (F)

Prepared as described for the example above. H$^1$ NMR (CDCl$_3$) δ 0.18 (2H, m), 0.51 (2H, m), 0.85 (3H, t), 0.95 (1H, m), 1.12 (3H, t), 1.58 (2H, m), 2.51 (2H, q), 3.27 (2H, d), 3.45 (2H, ABq), 7.43 (2H, s). Mass spec.: 448.06 (MH)$^+$.

Example 11

2-(2,4,6-Trichlorophenylamino)-5-(N-n-propyl-N-cyclopropylmethyl)aminocarbonyl-4-trifluoromethylthiazole, Scheme 1: (F)

Prepared as described for the example above. H$^1$ NMR (CDCl$_3$) δ 0.16 (1H, m), 0.24 (1H, m), 0.55 (0.83 (3H, m), 1.02 (1H, m), 1.59 (3H, m), 3.14 (1H, m), 3.36 (2H, m), 3.50 (1H, m), 7.47 (2H, s), 9.18 (1H, brs). Mass spec.: 486.03 (MH)$^+$.

Example 4

2-(2,4,6-Trichlorophenylamino)-5-(N,N-di-n-propyl)aminocarbonyl-4-methylthiazole, Scheme 3: (F)

Prepared as described for the example above. H$^1$ NMR (CDCl$_3$) δ 7.45 (2H, s), 3.37–3.27 (4H, m), 2.23 (3H, s), 1.65–1.53 (4H, m), 0.90–0.85 (6H, m).

Example 5

2-(2,4,6-Trichlorophenylamino)-5-(N-ethyl-N-n-butyl)aminocarbonyl-4-methylthiazole, Scheme 3: (F)

Prepared as described for the example above. H$^1$ NMR (CDCl$_3$) δ 7.44 (2H, s), 3.47–3.34 (4H, m), 2.20 (3H, s), 1.59–1.49 (2H, m), 1.34–1.22 (2H, m), 1.15 (3H, t, J=7.1 Hz), 0.90 (3H, t, J=7.3 Hz).

Example 7

2-(2,4,6-Trichlorophenylamino)-5-(N,N-bis-2-methoxyethyl)aminocarbonyl-4-methylthiazole, Scheme 3: (F)

Prepared as described for the example above. H$^1$ NMR (CDCl$_3$) δ 7.44 (2H, s), 3.69–3.66 (4H, m), 3.53–3.50 (4H, m), 3.31 (6H, s), 2.23 (3H, s).

Example 6

2-(2,4,6-Trichlorophenylamino)-5-(N,N-diethyl)aminocarbonyl-4-methylthiazole, Scheme 3: (F)

Prepared as described for the example above. H$^1$ NMR (CDCl$_3$) δ 7.44 (2H, s), 3.45 (4H, q, J=7.1 Hz), 2.22 (3H, s), 1.16 (6H, t, J=7.1 Hz).

Example 8

2-(2,4,6-Trichlorophenylamino)-5-(N-ethyl-N-2-methoxyethyl)aminocarbonyl-4-methylthiazole, Scheme 3: (F)

Prepared as described for the example above. H$^1$ NMR (CDCl$_3$) δ 7.44 (2H, s), 3.6$_{1-6}$.0.48 (6H, m), 3.33 (3H, s), 2.22 (3H, s), 1.15 (3H, t, J=7.1 Hz).

Example 12

2-(2,4,6-Trichlorophenylamino)-5-(N-n-propyl-N-cyclopropylmethyl)aminomethyl-4-trifluoromethylthiazole, Scheme 4: (K)

A stirred solution of 2-(2,4,6-Trichlorophenylamino)-5-(N-n-propyl-N-cyclopropylmethyl)aminocarbonyl-4-trifluoromethylthiazole (scheme 4: (F)) (144.6 mg, 0.297 mmoles) in dry tetrahydrofuran (2 mL) at 0° C. was treated with 1M diborane in tetrahydrofuran (1.3 mL, 4 equiv.). After a few minutes at room temperature, the mixture was heated at reflux for 16 hours. Upon re-cooling to 0° C., dry methanol (5 mL) was added. After stirring for 10 minutes, the solvents were removed in vacuo. The residue was dissolved in methanol (20 mL) and the mixture heated at reflux for 1 hour. Upon evaporation, the residue was purified by silica gel chromatography, eluting with 12% ethyl acetate/hexane, to give the product as a colorless oil that solidified upon standing (106.0 mg, 75%). $H^1$ NMR (CDCl$_3$) δ 0.05 (2H, q), 0.45 (2H, m), 0.84 (4H, t & m), 1.42 (2H, m), 2.34 (2H, d), 2.48 (2H, ABq), 3.75 (2H, d), 7.45 (2H, s), 8.42 (1H, brs). Mass spec.: 474.12 (MH)$^+$.

Example 3

2-(N-Ethyl-N-2,4,6-trichlorophenylamino)-5-(N-cyclopropylmethyl-N-n-propyl)aminocarbonyl-4-methylthiazole, Scheme 4: (J)

A solution of lithium hexamethyldisilazide (LiHMDS) (1M in hexanes, 0.19 mL, 0.19 mmoles) was added to 2-(2,4,6-trichlorophenylamino)-5-(N-cyclopropylmethyl-N-n-propyl)aminocarbonyl-4-methylthiazole (scheme 4: (F)) (20.2 mg, 0.047 mmoles) in tetrahydrofuran (1 mL). To this was added bromoethane (0.035 ml, 0.47 mmoles), and the reaction was stirred for 14 hours at 40° C. Ethyl acetate was added, and the solution was washed with saturated ammonium chloride and brine. The organic phase was dried over MgSO$_4$ and concentrated in vacuo. Purification via silica gel chromatography afforded 10 mg. $H^1$ NMR (CDCl$_3$) δ 7.53 (2H, s), 3.93 (2H, q, J=7.3 Hz), 3.50–3.45 (2H, m), 3.30 (2H, d, J=6.8 Hz), 2.30 (3H, s), 1.64–1.56 (3H, m), 1.25 (3H, t, J=7.3 Hz), 0.87 (3H, t, J=7.4 Hz), 0.56–0.50 (2H, m), 0.22–0.17 (2H, m).

Example 2

2-(N-Methyl-N-2,4,6-trichlorophenylamino)-5-(N-cyclopropylmethyl-N-n-propyl)aminocarbonyl-4-methylthiazole, Scheme 4: (J)

Prepared as described for the example above. □ □ $H^1$ NMR (CDCl$_3$) δ 7.53 (2H, s), 3.93 (2H, q, J=7.3 Hz), 3.50–3.45 (2H, m), 3.42 (3H, s), 3.30 (2H, d, J=6.8 Hz), 2.31 (3H, s), 1.64–1.54 (2H, m), 1.01–0.92 (1H, m), 0.87 (3H, t, J=7.4 Hz), 0.56–0.50 (2H, m), 0.22–0.17 (2H, m).

Example 9

2-(2,4,6-Trimethylphenylamino)-5-(N-n-propyl-N-cyclopropylmethyl)aminocarbonyl-4-methylthiazole, Scheme 2: (F)

In a sealed tube, a solution of 2-chloro-N-n-propyl-N-cyclopropylmethyl acetoacetamide (scheme 2: (I)) (74.0 mg, 0.257 mmoles) and 2,4,6-trimethylphenylthiourea (scheme 2: (A)) (50.0 mg, 0.257 mmoles) in ethanol (3 mL) was stirred at 80° C. for 2 hours. The solution was then cooled to room temperature and basified with a solution of ammonia in methanol. The solvents were removed in vacuo and the crude product purified via silica gel chromatography (1:2 ethyl acetate:hexane) to afford 82 mg (86%) of the product as a white solid. $H^1$ NMR (CDCl$_3$) δ 6.95 (2H, s), 3.45–3.40 (2H, t), 3.26 (2H, d, J=6.84 Hz), 3.01 (3H, s), 2.30 (6H, s), 2.24 (3H, s), 1.60–1.50 (2H, m), 0.96–0.87 (1H, m), 0.83 (3H, t, J=7.3, 14.7 Hz), 0.52–0.49 (2H, m), 0.17–0.15 (2H, m).

Example 13

2-(2,4,6-Trimethylphenylamino)-5-(N-n-propyl-N-cyclopropylmethyl)aminocarbonyl-4-methyloxazole, Scheme 1: (F)

A solution of cyclopropylmethylpropylamine (scheme 1: (E)) (0.281 mL, 4 equiv.) in dry benzene (2 mL) under argon at 0° C. was treated with a 2M solution of trimethylaluminum in toluene (0.98 mL, 4 equiv.). The mixture was warmed to room temperature, stirred for 1.5 h, and then treated with a solution of 2-(2,4,6-trimethylphenylamino)-5-ethoxycarbonyl-4-methyloxazole (scheme 1: (D)) (141.7 mg, 0.4915 mmoles) in dry benzene (2.5 mL). The mixture was heated at reflux for 18 hours. Upon cooling to room temperature, the mixture was carefully quenched with 5% hydrochloric acid and extracted three times with ethyl acetate. The organic phase was washed with water and brine, dried over magnesium sulfate, and evaporated. The residue was purified by silica gel chromatography, eluting with 2:1 ethyl acetate/hexane, to give the product as a pale-yellow solid (138.9 mg, 80%). $^1$H-NMR (CDCl$_3$) δ 0.06 (2H, br), 0.38 (2H, br), 0.5–1.1 (4H, br m), 1.42 (2H, m), 2.22 (6H, s), 2.25 (3H, s), 2.32 (3H, s), 3.17 (2H, br d), 3.24 (2H, br q), 6.90 (2H, s), 7.93 (1H, br). Mass spec.: 356.22 (MH$^+$).

Example 14

2-(2-Chloro-4,6-dimethylphenylamino)-5-(N-n-propyl-N-cyclopropylmethyl)aminocarbonyl-4-methyloxazole, Scheme 1: (F)

Prepared as described for the example above. $^1$H-NMR (CDCl$_3$) □ 0.05 (2H, br), 0.39 (2H, br), 0.5–1.1 (4H, br m), 1.43 (2H, m), 2.28 (3H, s), 2.29 (6H, s), 3.19 (2H, d), 3.31 (2H, ABq), 6.98 (1H, s), 7.12 (1H, s), 8.68 (1H, br). Mass spec.: 376.64 (MH$^+$).

SECOND SET OF EXAMPLES

Preparation of Compounds of Formula (I)

Example 1

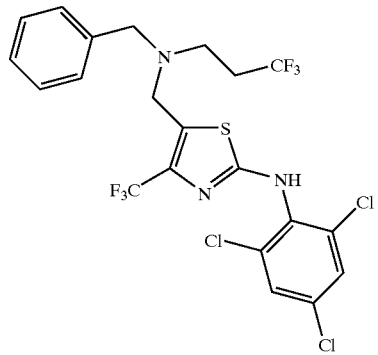

(5-{[Benzyl-(3,3,3-trifluoropropyl)-amino]-methyl}-4-trifluoromethylthiazol-2-yl)-(2,4,6-trichlorophenyl)-amine, Scheme 6 (K)

A stirred suspension of benzyl-3,3,3-trifluoropropyl-amine hydrochloride (152.8 mg, 3 equiv.) in methylene chloride (10 mL) at room temperature was treated with diisopropylethylamine (0.132 mL, 3 equiv.). Within a few minutes the mixture became homogeneous and then a 12.5 mg/mL solution of (5-chloromethyl-4-trifluoromethyl-thiazol-2-yl)-(2,4,6-trichloro-phenyl)-amine in ether (8 mL, 0.2525 mmoles) was added all at once. After 12 hours at room temperature, the mixture was evaporated and the residue partitioned between ethyl acetate and water. The organic phase was washed with brine, dried over sodium sulfate and evaporated. The residue was chromatographed on silica gel, eluting with 12% ethyl acetate/hexane, to give the product as a colorless glass (133.6 mg, 94%). $^1$H-NMR δ (CDCl$_3$) 2.27 (m, 2H), 2.75 (ABq, 2H), 3.62 (s, 2H), 3.74 (s, 2H), 7.28 (m, 5H), 7.48 (s, 2H), 8.75 (br, 1H). Mass spec.: 563.98 (MH$^+$).

Similarly prepared:

Example 2

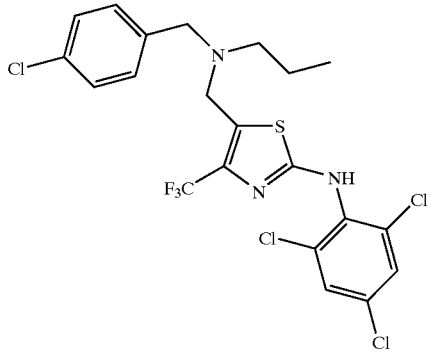

(5-{[(4-Chlorobenzyl)-propyl-amino]-methyl}-4-trifluoromethylthiazol-2-yl)-(2,4,6-trichlorophenyl)-amine, Scheme 6 (K)

$^1$H-NMR δ (CDCl$_3$) 0.83 (t, 3H), 1.47 (m, 2H), 2.39 (t, 2H), 3.53 (s, 2H), 3.67 (s, 2H), 7.25 (m, 4H), 7.47 (s, 2H). Mass spec.: 544.46 (MH$^+$).

Example 3

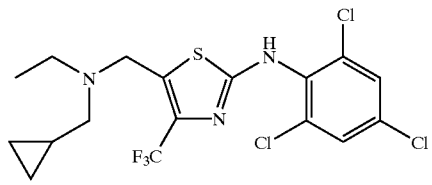

{5-[(Cyclopropylmethyl-ethyl-amino)-methyl]-4-trifluoromethyl-thiazol-2-yl}-(2,4,6-trichloro-phenyl)-amine, Scheme 6(K)

Mass spec.: 458.07 (MH$^+$).

Example 4

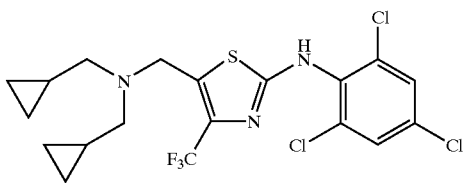

{5-[(Bis-cyclopropylmethyl-amino)-methyl]-4-trifluoromethyl-thiazol-2-yl}-(2,4,6-trichloro-phenyl)-amine, Scheme 6 (K)

Mass spec.: 484.08 (MH$^+$).

Example 5

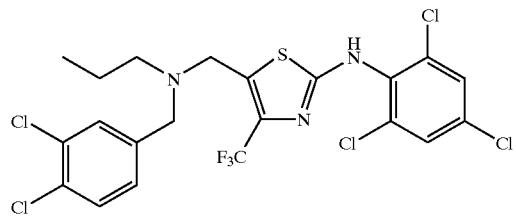

(5-{[(3,4-Dichloro-benzyl)-propyl-amino]-methyl}-4-trifluoromethyl-thiazol-2-yl)-(2,4,6-trichloro-phenyl)-amine, Scheme 6 (K)

Mass spec.: 576.05 (MH$^+$).

Example 6

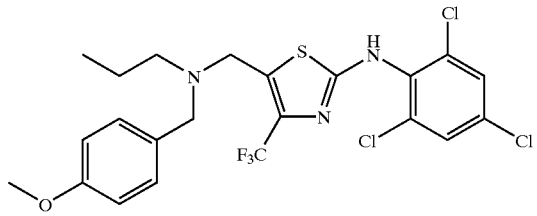

(5-{[(4-Methoxy-benzyl)-propyl-amino]-methyl}-4-trifluoromethyl-thiazol-2-yl)-(2,4,6-trichloro-phenyl)-amine, Scheme 6 (K)

Mass spec.: 538.10 (MH$^+$).

Example 7

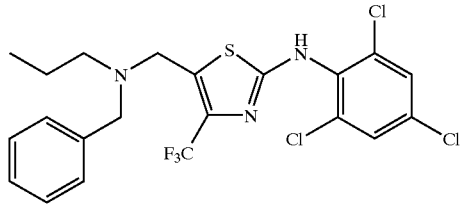

{5-[(Benzyl-propyl-amino)-methyl]-4-trifluoromethyl-thiazol-2-yl}-(2,4,6-trichloro-phenyl)-amine, Scheme 6(K)

Mass spec.: 507.95 (MH$^+$).

Example 8

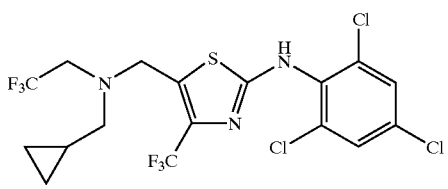

(5-{[Cyclopropylmethyl-(2,2,2-trifluoro-ethyl)-amino]-methyl}-4-trifluoromethyl-thiazol-2-yl)-(2,4,6-trichloro-phenyl)-amine, Scheme 6 (K)

Mass spec.: 512.03 (MH$^+$).

Example 9

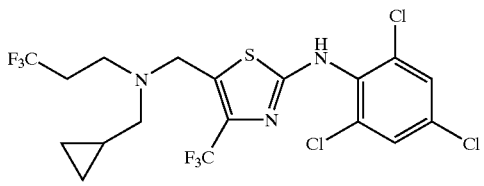

(5-{[Cyclopropylmethyl-(3,3,3-trifluoro-propyl)-amino]-methyl}-4-trifluoromethyl-thiazol-2-yl)-(2,4,6-trichloro-phenyl)-amine, Scheme 6 (K)

Mass spec.: 526.04 (MH$^+$).

Example 10

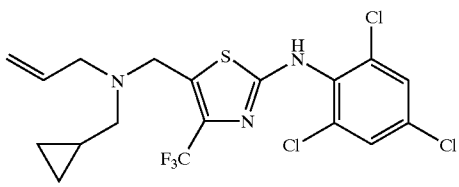

{5-[(Allyl-cyclopropylmethyl-amino)-methyl]-4-trifluoromethyl-thiazol-2-yl}-(2,4,6-trichloro-phenyl)-amine, Scheme 6 (K)

Mass spec.: 470.00 (MH$^+$).

Example 11

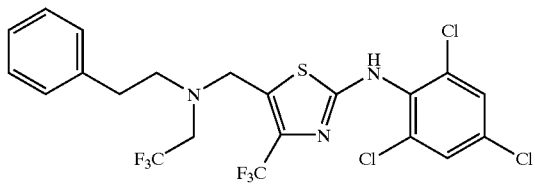

(5-{[Phenethyl-(2,2,2-trifluoro-ethyl)-amino]-methyl}-4-trfluoromethyl-thiazol-2-yl)-(2,4,6-trichloro-phenyl)-amine, Scheme 6 (K)

Mass spec.: 562.06 (MH$^+$).

Example 12

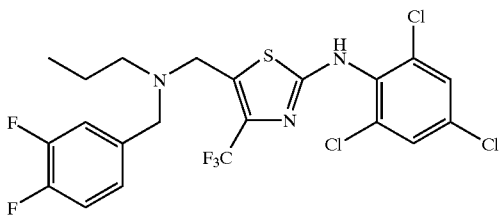

(5-{[(3,4-Difluoro-benzyl)-propyl-amino]-methyl}-4-trifluoromethyl-thiazol-2-yl)-(2,4,6-trichloro-phenyl)-amine, Scheme 6 (K)

Mass spec.: 544.04 (MH$^+$).

Example 13

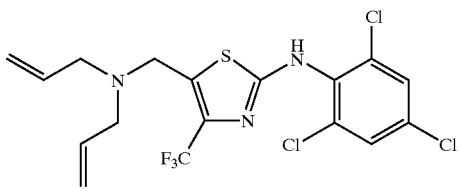

(5-Diallylaminomethyl-4-trifluoromethyl-thiazol-2-yl)-(2,4,6-trichloro-phenyl)-amine, Scheme 6 (K)

Mass spec.: 455.96 (MH$^+$).

Example 14

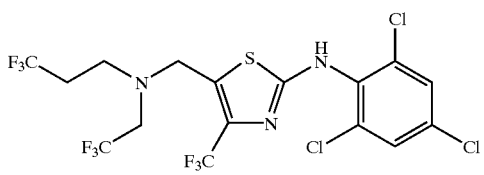

(2,4,6-Trichloro-phenyl)-(5-{[(2,2,2-trifluoro-ethyl)-(3,3,3-trifluoro-propyl)-amino]-methyl}-4-trifluoromethyl-thiazol-2-yl)-amine, Scheme 6 (K)

Mass spec.: 554.00 (MH$^+$).

Example 15

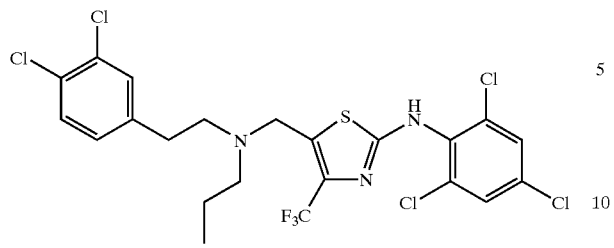

[5-({[2-(3,4-Dichloro-phenyl)-ethyl]-propyl-amino}-methyl)-4-trifluoromethyl-thiazol-2-yl]-(2,4,6-trichloro-phenyl)-amine, Scheme 6 (K)

Mass spec.: 590.01 (MH$^+$).

Example 16

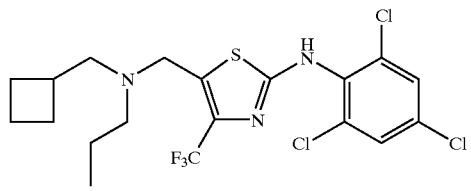

{5-[(Cyclobutylmethyl-propyl-amino)-methyl]-4-trifluoromethyl-thiazol-2-yl}-(2,4,6-trichloro-phenyl)-amine, Scheme 6 (K)

Mass spec.: 486.05 (MH$^+$).

Example 17

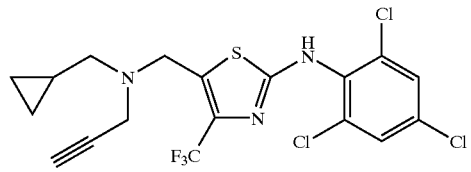

{5-[(Cyclopropylmethyl-prop-2-ynyl-amino)-methyl]-4-trifluoromethyl-thiazol-2-yl}-(2,4,6-trichloro-phenyl)-amine, Scheme 6 (K)

Mass spec.: 467.95 (MH$^+$).

Example 18

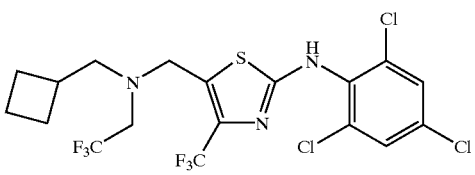

(5-{[Cyclobutylmethyl-(2,2,2-trifluoro-ethyl)-amino]-methyl}-4-trifluoromethyl-thiazol-2-yl)-(2,4,6-trichloro-phenyl)-amine, Scheme 6 (K)

Mass spec.: 526.06 (MH$^+$).

Example 19

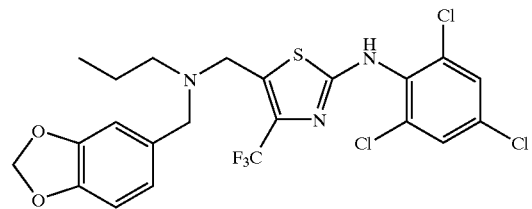

{5-[(Benzo[1,3dioxol-5-ylmethyl-propyl-amino)-methyl]-4-trifluoromethyl-thiazol-2-yl}-(2,4,6-trichloro-phenyl)-amine, Scheme 6 (K)

Mass spec.: 552.11 (MH$^+$).

Example 20

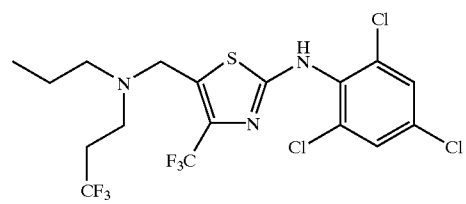

(5-{[Propyl-(3,3,3-trifluoro-propyl)-amino]-methyl}-4-trifluoromethyl-thiazol-2-yl)-(2,4,6-trichloro-phenyl)-amine, Scheme 6 (K)

Mass spec.: 514.01 (MH$^+$).

Example 21

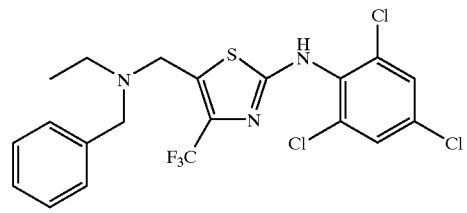

{5-[(Benzyl-ethyl-amino)-methyl]-4-trifluoromethyl-thiazol-2-yl}(2,4,6-trichloro-phenyl)-amine, Scheme 6 (K)

Mass spec.: 493.94 (MH$^+$).

Example 22

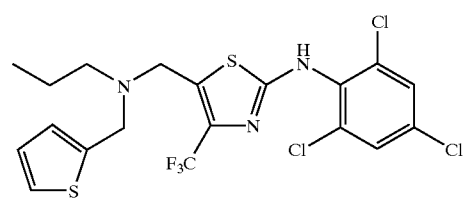

{5-[(Propyl-thiophen-2-ylmethyl-amino)-methyl]-4-trifluoromethyl-thiazol-2-yl-(2,4,6-trichloro-phenyl)-amine, Scheme 6 (K)

Mass spec.: 514.05 (MH$^+$).

Example 23

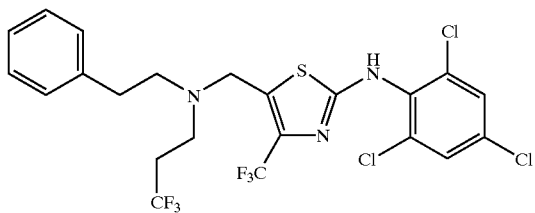

(5-{[Phenethyl-(3,3,3-trifluoro-propyl)-amino]-methyl}-4-trifluoromethyl-thiazol-2-yl)-(2,4,6-trichloro-phenyl)-amine, Scheme 6 (K)

Mass spec.: 576.07 (MH$^+$).

Example 24

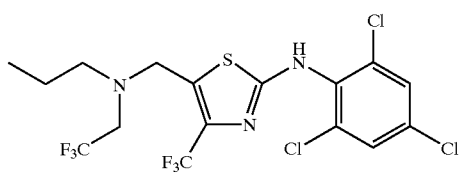

(5-{[Propyl-(2,2,2-trifluoro-ethyl)-amino]-methyl}-4-trifluoromethyl-thiazol-2-yl)-(2,4,6-trichloro-phenyl)-amine, Scheme 6 (K)

Mass spec.: 500.02 (MH$^+$).

Example 25

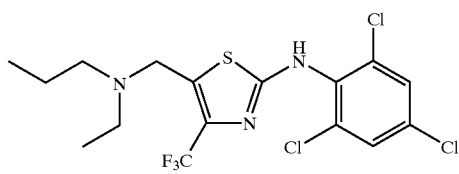

{5-[(Ethyl-propyl-amino)-methyl]-4-trifluoromethyl-thiazol-2-yl}-(2,4,6-trichloro-phenyl)-amine, Scheme 6 (K)

Mass spec.: 446.03 (MH$^+$).

Example 26

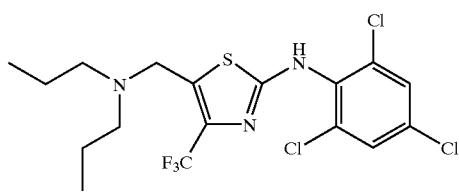

(5-Dipropylaminomethyl-4-trifluoromethyl-thiazol-2-yl)-(2,4,6-trichloro-phenyl)-amine, Scheme 6 (K)

Mass spec.: 459.98 (MH$^+$).

Example 27

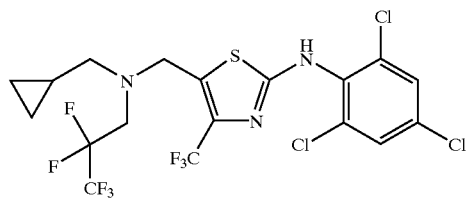

(5-{[Cyclopropylmethyl-(2,2,3,3,3-pentafluoro-propyl)-amino]-methyl}-4-trifluoromethyl-thiazol-2-yl)-(2,4,6-trichloro-phenyl)-amine, Scheme 6 (K)

Mass spec.: 561.98 (MH$^+$).

Example 28

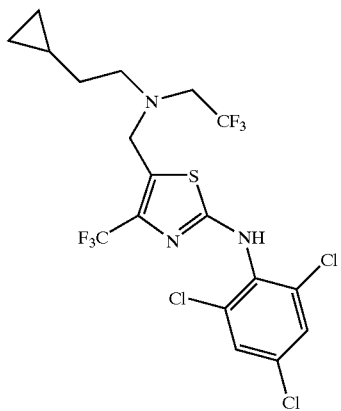

(5-{[(2-Cyclopropyl-ethyl)-(2,2,2-trifluoro-ethyl)-amino]-methyl}-4-trifluoromethyl-thiazol-2-yl)-(2,4,6-trichloro-phenyl)-amine, Scheme 6 (K)

$^1$H-NMR δ (CDCl$_3$) −0.01 (m, 2H), 0.38 (m, 2H), 0.60 (m, 1H), 1.32 (m, 2H), 2.71 (ABq, 2H), 3.09 (q, 2H), 3.94 (s, 2H), 7.45 (s, 2H), 7.95 (brs, 1H). Mass spec.: 527.87 (MH$^+$).

Example 29

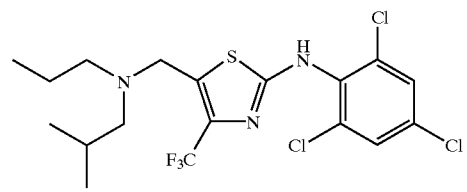

{5-[(Isobutyl-propyl-amino)-methyl]-4-trifluoromethyl-thiazol-2-yl}-(2,4,6-trichloro-phenyl)-amine, Scheme 6 (K)

Mass spec.: 474.13 (MH$^+$).

Example 30

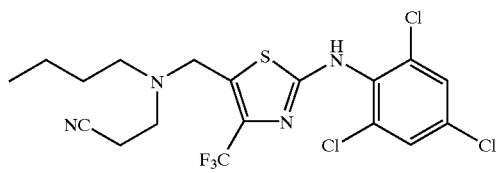

3-{Butyl-[2-(2,4,6-trichloro-phenylamino)-4-trifluoromethyl-thiazol-5-ylmethyl]-amino}-propionitrile, Scheme 6 (K)

Mass spec.: 484.97 (MH⁺).

Example 31

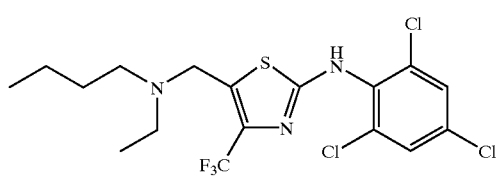

{5-[(Butyl-ethyl-amino)-methyl]-4-trifluoromethyl-thiazol-2-yl}-(2,4,6-trichloro-phenyl)-amine, Scheme 6 (K)

Mass spec.: 459.99 (MH⁺).

Example 32

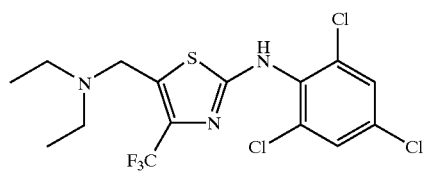

(5-Diethylaminomethyl-4-trifluoromethyl-thiazol-2-yl)-(2,4,6-trichloro-phenyl)-amine, Scheme 6 (K)

Mass spec.: 432.09 (MH⁺).

Example 33

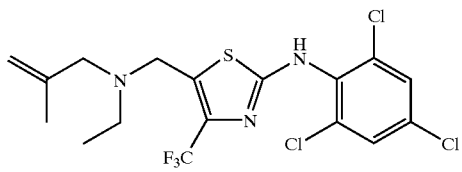

(5-{[Ethyl-(2-methyl-allyl)-amino]-methyl}-4-trifluoromethyl-thiazol-2-yl)-(2,4,6-trichloro-phenyl)-amine, Scheme 6 (K)

Mass spec.: 457.98 (MH⁺).

Example 34

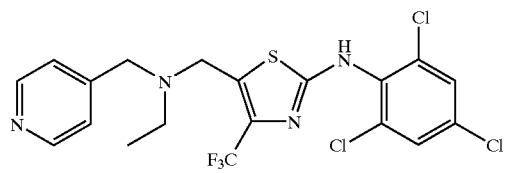

{5-[(Ethyl-pyridin-4-ylmethyl-amino)-methyl]-4-trifluoromethyl-thiazol-2-yl}-(2,4,6-trichloro-phenyl)-amine, Scheme 6 (K)

Mass spec.: 494.96 (MH⁺).

Example 35

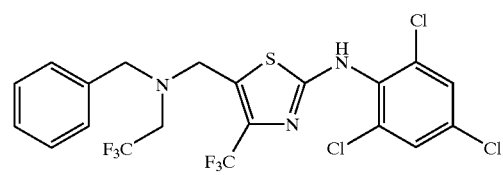

(5-{[Benzyl-(2,2,2-trifluoro-ethyl)-amino]-methyl}-4-trifluoromethyl-thiazol-2-yl)-(2,4,6-trichloro-phenyl)-amine, Scheme 6 (K)

Mass spec.: 548.02 (MH⁺).

Example 36

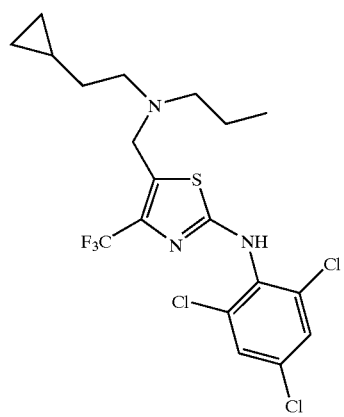

(5-{[(2-Cyclopropyl-ethyl)-propyl-amino]-methyl}-4-trifluoromethyl-thiazol-2-yl)-(2,4,6-trichloro-phenyl)-amine, Scheme 6 (K)

$^1$H-NMR δ (CDCl$_3$) −0.02 (m, 2H), 0.36 (m, 2H), 0.61 (m, 1H), 1.29 (m, 2H), 1.40 (m, 2H), 2.38 (ABq, 2H), 2.52 (ABq, 2H), 3.66 (s, 2H), 7.44 (s, 2H), 7.96 (br, 1H). Mass spec.: 488.02 (MH⁺).

Example 37

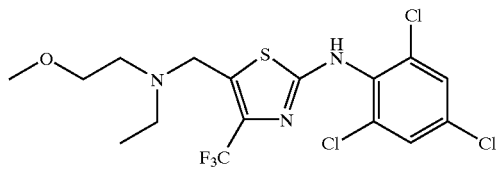

(5-{[Ethyl-(2-methoxy-ethyl)-amino]-methyl}-4-trifluoromethyl-thiazol-2-yl)-(2,4,6-trichloro-phenyl)-amine, Scheme 6 (K)

Mass spec.: 461.93 (MH$^+$).

Example 38

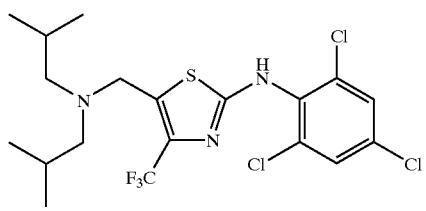

{5-[(Diisobutylamino)-methyl]-4-trifluoromethyl-thiazol-2-yl}-(2,4,6-trichloro-phenyl)-amine, Scheme 6 (K)

Mass spec.: 488.00 (MH$^+$).

Example 39

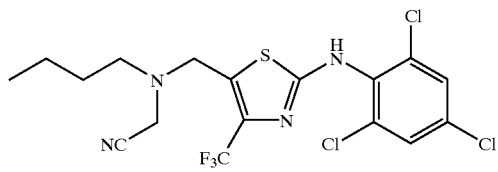

{Butyl-[2-(2,4,6-trichloro-phenylamino)-4-trifluoromethyl-thiazol-5-ylmethyl]-amino}-acetonitrile, Scheme 6 (K)

Mass spec.: 471.03 (MH$^+$).

Example 40

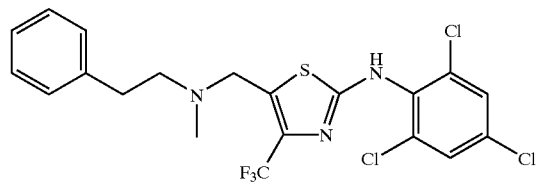

{5-[(Methyl-phenethyl-amino)-methyl]-4-trifluoromethyl-thiazol-2-yl}-(2,4,6-trichloro-phenyl)-amine, Scheme 6 (K)

Mass spec.: 493.94 (MH$^+$).

Example 41

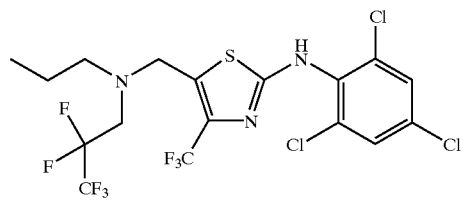

(5-{[(2,2,3,3,3-Pentafluoro-propyl)-propyl-amino]-methyl}-4-trifluoromethyl-thiazol-2-yl)-(2,4,6-trichloro-phenyl)-amine, Scheme 6 (K)

Mass spec.: 550.04 (MH$^+$).

Example 42

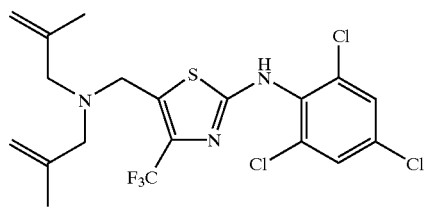

(5-{[Bis-(2-methyl-allyl)-amino]-methyl}-4-trifluoromethyl-thiazol-2-yl)-(2,4,6-trichloro-phenyl)-amine, Scheme 6 (K)

Mass spec.: 483.97 (MH$^+$).

Example 43

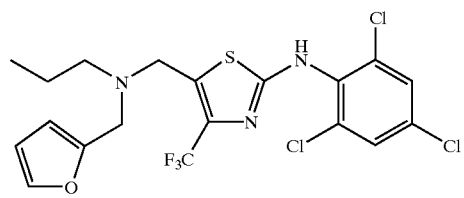

{5-[(Furan-2-ylmethyl-propyl-amino)-methyl]-4-trifluoromethyl-thiazol-2-yl}-(2,4,6-trichloro-phenyl)-amine, Scheme 6 (K)

Mass spec.: 498.05 (MH$^+$).

Example 44

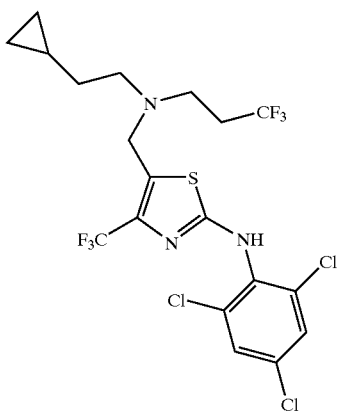

(5-{[(2-Cyclopropyl-ethyl)-(3,3,3-trifluoro-propyl)-amino]-methyl}-4-trifluoromethyl-thiazol-2-yl)-(2,4,6-trichloro-phenyl)-amine, Scheme 6 (K)

$^1$H-NMR δ (CDCl$_3$) −0.01 (m, 2H), 0.40 (m, 2H), 0.61 (m, 1H), 1.31 (m, 2H), 2.22 (m, 2H), 2.55 (ABq, 2H), 2.70 (ABq, 2H), 3.71 (s, 2H), 7.45 (s, 2H), 8.04 (brs, 1H). Mass spec.: 541.99 (MH$^+$).

Example 45

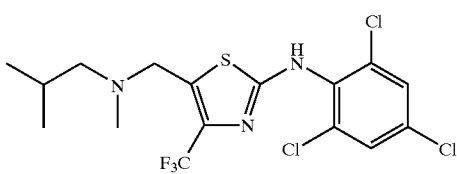

{5-[(Isobutyl-methyl-amino)-methyl]-4-trifluoromethyl-thiazol-2-yl}-(2,4,6-trichloro-phenyl)-amine, Scheme 6 (K)

Mass spec.: 445.96 (MH$^+$).

Example 46

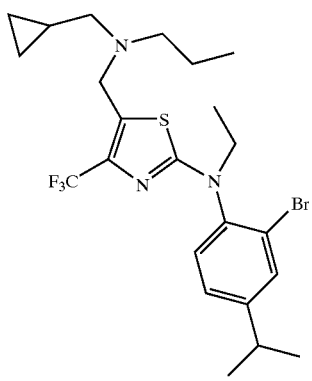

(2-Bromo-4-isopropyl-phenyl)-{5-[(cyclopropylmethyl-propyl-amino)-methyl]-4-trifluoromethylthiazol-2-yl}-ethyl-amine, Scheme 4 (L)

$^1$H-NMR δ (CDCl$_3$) 0.03 (m, 2H), 0.44 (m, 2H), 0.79 (m, 1H), 0.82 (t, 3H), 1.20 (t, 3H), 1.27 (s, 3H), 1.29 (s, 3H), 1.41 (m, 2H), 2.32 (d, 2H), 2.47 (ABq, 2H), 2.93 (m, 1H), 3.73 (s, 2H), 3.94 (brm, 1H), 7.24 (s, 2H), 7.56 (s, 1H). Mass spec.: 519.71 (MH$^+$).

Example 47

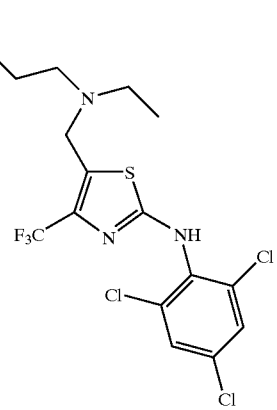

(5-{[(2-Cyclopropyl-ethyl)-ethyl-amino]-methyl}-4-trifluoromethyl-thiazol-2-yl)-(2,4,6-trichloro-phenyl)-amine: Scheme 6 (K)

$^1$H-NMR δ (CDCl$_3$) 0.01 (m, 2H), 0.36 (m, 2H), 0.61 (m, 1H), 0.99 (t, 3H), 1.29 (q, 2H), 2.52 (m, 4H), 3.67 (s, 2H), 7.44 (s, 2H), 7.96 (br, 1H). Mass spec.: 474.00 (MH$^+$).

Example 48

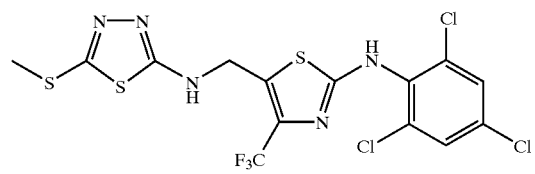

(5-Methylsulfanyl-[1,3,4]thiadiazol-2-yl)-[2-(2,4,6-trichloro-phenylamino)-4-trifluoromethyl-thiazol-5-ylmethyl]-amine, Scheme 6 (K)

Mass spec.: 520.02 (MH$^+$).

Example 49

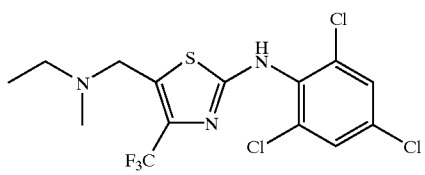

{5-[(Ethyl-methyl-amino)-methyl]-4-trifluoromethyl-thiazol-2-yl}-(2,4,6-trichloro-phenyl)amine, Scheme 6 (K)

Mass spec.: 417.90 (MH$^+$).

Example 50

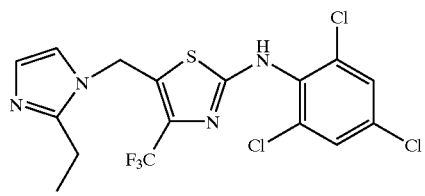

[5-(2-Ethyl-imidazol-1-ylmethyl)-4-trifluoromethyl-
thiazol-2-yl]-(2,4,6-trichloro-phenyl)-amine,
Scheme 6 (K)

Mass spec.: 454.93 (MH$^+$).

Example 51

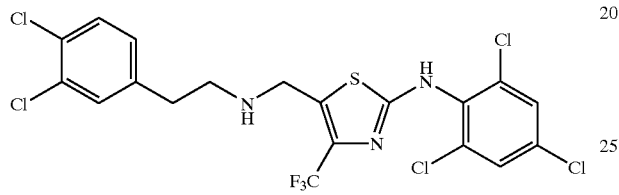

(5-{[2-(3,4-Dichloro-phenyl)-ethylamino]-methyl}-
4-trifluoromethyl-thiazol-2-yl)-(2,4,6-trichloro-
phenyl)amine, Scheme 6 (K)

Mass spec.: 547.86 (MH$^+$).

Example 52

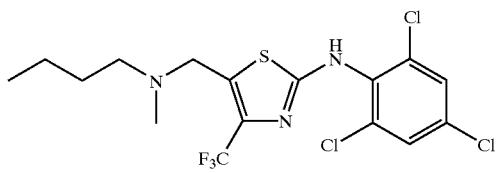

{5-[(Butyl-methyl-amino)-methyl]-4-
trifluoromethyl-thiazol-2-yl}-(2,4,6-trichloro-
phenyl)-amine, Scheme 6 (K)

Mass spec.: 445.96 (MH$^+$).

Example 53

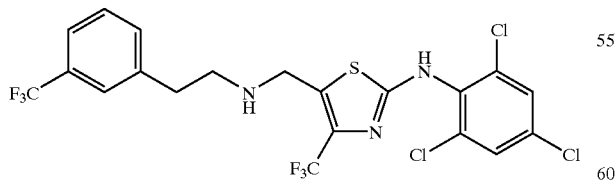

(2,4,6-Trichloro-phenyl)-(4-trifluoromethyl-5-{[2-
(3-trifluoromethyl-phenyl)-ethylamino]-methyl}-
thiazol-2-yl)-amine, Scheme 6 (K)

Mass spec.: 547.95 (MH$^+$).

Example 54

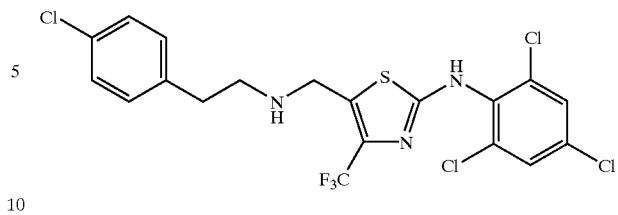

{5-[(4-Chloro-benzylamino)-methyl]-4-
trifluoromethyl-thiazol-2-yl}-(2,4,6-trichloro-
phenyl)-amine, Scheme 6 (K)

Mass spec.: 498.95 (MH$^+$).

Example 55

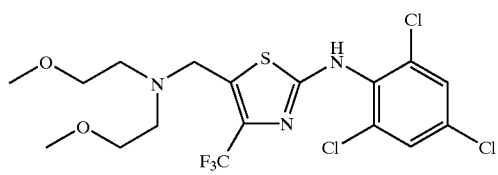

(5-[Bis-(2-methoxy-ethyl)-amino]-methyl}-4-
trifluoromethyl-thiazol-2-yl)-(2,4,6-trichloro-
phenyl)-amine, Scheme 6 (K)

Mass spec.: 491.94 (MH$^+$).

Example 56

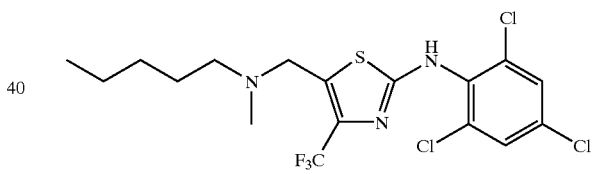

{5-[(Methyl-pentyl-amino)-methyl]-4-
trifluoromethyl-thiazol-2-yl}-(2,4,6-trichloro-
phenyl)-amine, Scheme 6 (K)

Mass spec.: 459.99 (MH$^+$).

Example 57

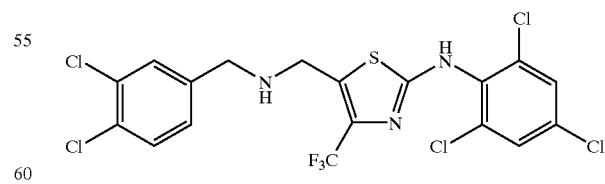

{5-[(3,4-Dichloro-benzylamino)-methyl]-4-
trifluoromethyl-thiazol-2-yl}-(2,4,6-trichloro-
phenyl)-amine, Scheme 6 (K)

Mass spec.: 533.92 (MH$^+$).

Example 58

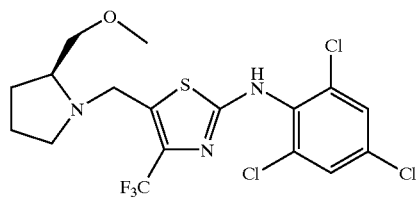

[5-(2-Methoxymethyl-pyrrolidin-1-ylmethyl)-4-
trifluoromethyl-thiazol-2-yl]-(2,4,6-trichloro-
phenyl)-amine, Scheme 6 (K)

Mass spec.: 473.91 (MH$^+$).

Example 59

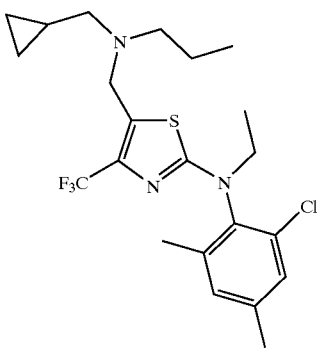

(2-Chloro-4,6-dimethyl-phenyl)-{5-
[(cyclopropylmethyl-propyl-amino)-methyl]-4-
trifluoromethylthiazol-2-yl}-ethyl-amine, Scheme 4
(L)

$^1$H-NMR δ (CDCl$_3$) 0.03 (m, 2H), 0.42 (m, 2H), 0.78 (m, 1H), 0.81 (t, 3H), 1.18 (t, 3H), 1.42 (m, 2H), 2.24 (s, 3H), 2.30 (ABq, 2H), 2.43 (s, 3H), 2.46 (ABq, 2H), 3.72 (s, 2H), 3.90 (m, 2H), 7.03 (s, 1H), 7.17 (s, 1H). Mass spec.: 461.23 (MH$^+$).

Example 60

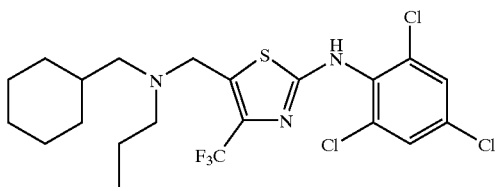

{5-[(Cyclohexylmethyl-propyl-amino)-methyl]-4-
trifluoromethyl-thiazol-2-yl}-(2,4,6-trichloro-
phenyl)-amine, Scheme 6 (K)

Mass spec.: 514.06 (MH$^+$).

Example 61

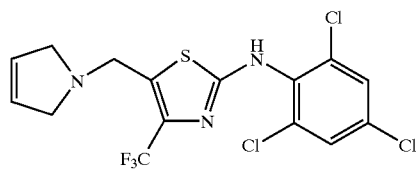

[5-(2,5-Dihydro-pyrrol-1-ylmethyl)-4-
trifluoromethyl-thiazol-2-yl]-(2,4,6-trichloro-
phenyl)-amine, Scheme 6 (K)

Mass spec.: 427.97 (MH$^+$).

Example 62

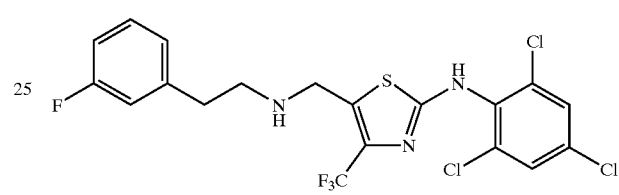

(5-{[2-(3-Fluoro-phenyl)-ethylamino]-methyl}-4-
trifluoromethyl-thiazol-2-yl)-(2,4,6-trichloro-
phenyl)-amine, Scheme 6 (K)

Mass spec.: 497.94 (MH$^+$).

Example 63

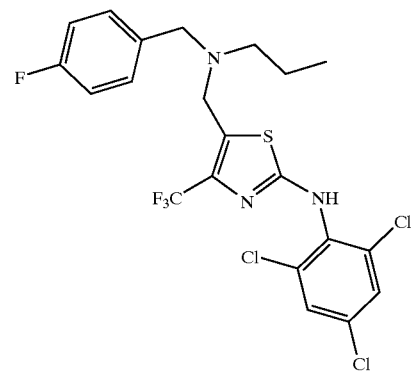

(5-{[(4-Fluorobenzyl)-propyl-amino]-methyl}-4-
trifluoromethylthiazol-2-yl)-(2,4,6-trichlorophenyl)-
amine, Scheme 6 (K)

$^1$H-NMR δ (CDCl$_3$) 0.83 (t, 3H), 1.47 (m, 2H), 2.39 (t, 2H), 3.53 (s, 2H), 3.66 (s, 2H), 6.99 (t, 2H), 7.23 (ABq, 2H), 7.47 (2H), 7.66 (br, 1H). Mass spec.: 528.04 (MH$^+$).

Example 64

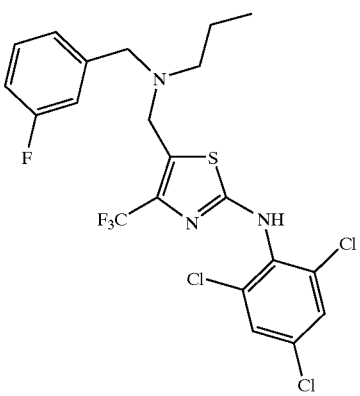

(5-{(3-Fluorobenzyl)-propyl-amino]-methyl}-4-trifluoromethylthiazol-2-yl)-(2,4,6-trichlorophenyl)-amine, Scheme 6 (K)

¹H-NMR δ (CDCl₃) 0.83 (t, 3H), 1.48 (m, 2H), 2.41 (ABq, 2H), 3.57 (s, 2H), 3.69 (s, 2H), 6.91 (m, 1H), 6.96 (m, 2H), 7.23 (t, 1H), 7.47 (s, 2H). Mass spec.: 528.05 (MH⁺).

Example 65

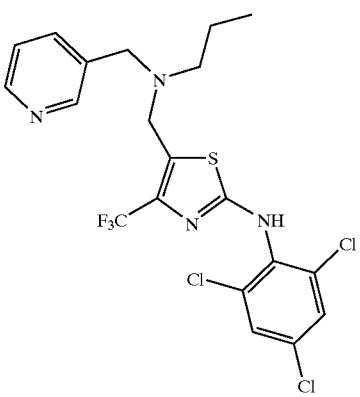

{5-[(Propyl-pyridin-3-ylmethyl-amino)-methyl]-4-trifluoromethylthiazol-2-yl}-(2,4,6-trichlorophenyl)-amine, Scheme 6 (K)

¹H-NMR δ (CDCl₃) 0.82 (t, 3H), 1.47 (m, 2H), 2.39 (t, 2H), 3.58 (s, 2H), 3.70 (s, 2H), 7.22 (ABq, 1H), 7.47 (s, 2H), 7.59 (d, 1H), 8.05 (br, 1H), 8.48 (d, 1H), 8.53 (s, 1H). Mass spec.: 511.08 (MH⁺).

Example 66

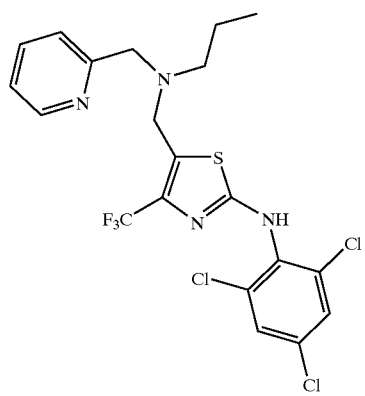

{5-[(Propyl-pyridin-2-ylmethyl-amino)-methyl]-4-trifluoromethylthiazol-2-yl}-(2,4,6-trichlorophenyl)-amine, Scheme 6 (K)

¹H-NMR δ (CDCl₃) 0.82 (t, 3H), 1.47 (m, 2H), 2.46 (t, 2H), 3.74 (d, 4H), 7.14 (ABq, 1H), 7.39 (d, 1H), 7.45 (s, 2H), 7.62 (t, 1H), 8.48 (d, 1H). Mass spec.: 511.06 (MH⁺).

Example 67

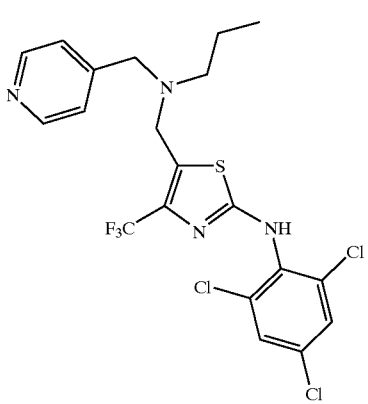

{5-[(Propyl-pyridin-4-ylmethyl-amino)-methyl]-4-trifluoromethylthiazol-2-yl}-(2,4,6-trichlorophenyl)-amine, Scheme 6 (K)

¹H-NMR δ (CDCl₃) 0.83 (t, 3H), 1.46 (m, 2H), 2.39 (t, 2H), 3.57 (s, 2H), 3.69 (s, 2H), 7.22 (d, 2H), 7.47 (s, 2H), 8.31 (br, 1H), 8.51 (d, 2H). Mass spec.: 511.07 (MH⁺).

Example 68

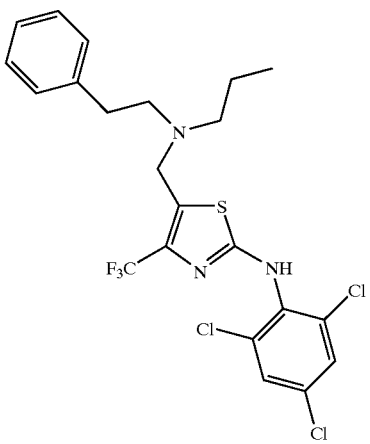

{5-[(Phenethyl-propyl-amino)-methyl]-4-trifluoromethylthiazol-2-yl}-(2,4,6-trichlorophenyl)-amine, Scheme 6 (K)

$^1$H-NMR δ (CDCl$_3$) 0.85 (t, 3H), 1.45 (m, 2H), 2.48 (ABq, 2H), 2.70 (s, 4H), 3.74 (s, 2H), 7.12 (m, 3H), 7.17 (d, 2H), 7.46 (s, 2H), 7.99 (brs, 1H). Mass spec.: 522.32 (MH$^+$).

Example 69

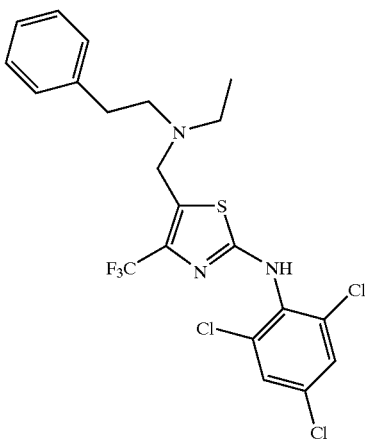

{5-[(Phenethyl-ethyl-amino)-methyl]-4-trifluoromethylthiazol-2-yl}-(2,4,6-trichlorophenyl)-amine, Scheme 6 (K)

$^1$H-NMR δ (CDCl$_3$) 1.02 (t, 3H), 2.62 (m, 2H), 2.71 (s, 4H), 3.74 (s, 2H), 7.12 (m, 3H), 7.22 (d, 2H), 7.46 (s, 2H), 8.09 (br, 1H). Mass spec.: 510.08 (MH$^+$).

Example 70

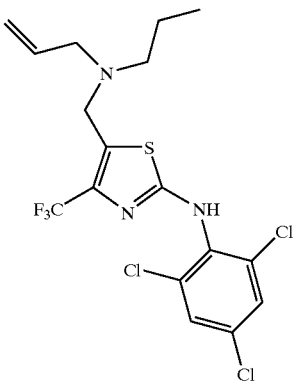

{5-[(Allyl-propyl-amino)-methyl]-4-trifluoromethylthiazol-2-yl}-(2,4,6-trichlorophenyl)-amine, Scheme 6 (K)

$^1$H-NMR δ (CDCl$_3$) 0.84 (t, 3H), 5 1.42 (m, 2H), 2.41 (ABq, 2H), 3.08 (d, 2H), 3.68 (s, 2H), 5.15 (m, 2H), 5.75 (m, 1H), 7.45 (s, 2H), 7.79 (brs, 1H). Mass spec.: 460.01 (MH$^+$).

Example 71

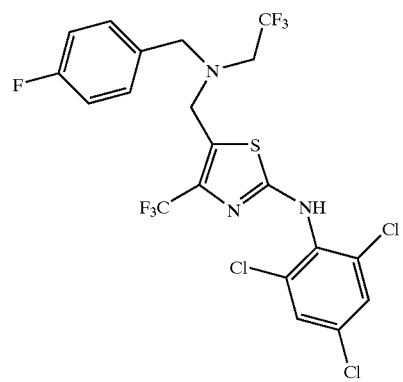

(5-{[(4-Fluorobenzyl)-(2,2,2-trifluoroethyl)-amino]-methyl}-4-trifluoromethylthiazol-2-yl)-(2,4,6-trichlorophenyl)-amine, Scheme 6 (K)

$^1$H-NMR δ (CDCl$_3$) 3.08 (q, 2H), 3.75 (s, 2H), 3.95 (s, 2H), 7.00 (t, 2H), 7.24 (ABq, 2H), 7.49 (s, 2H), 8.31 (br, 1H). Mass spec.: 567.97 (MH$^+$).

Example 72

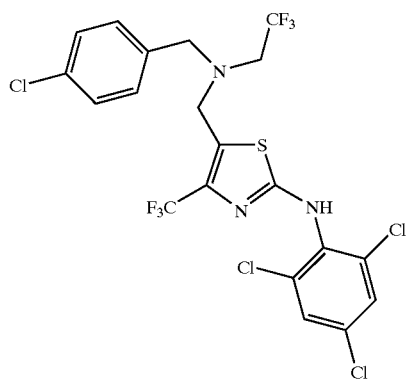

(5-{[(4-Chlorobenzyl)-(2,2,2-trifluoroethyl)-amino]-methyl}-4-trifluoromethylthiazol-2-yl)-(2,4,6-trichlorophenyl)-amine, Scheme 6 (K)

$^1$H-NMR δ (CDCl$_3$) 3.09 (q, 2H), 3.76 (s, 2H), 3.97 (s, 2H), 7.26 (q, 4H), 7.48 (s, 2H), 7.94 (br, 1H). Mass spec.: 584.46 (MH$^+$).

Example 73

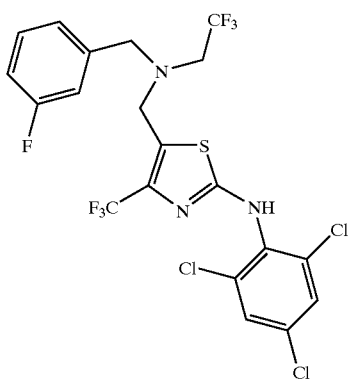

(5-{[(3-Fluorobenzyl)-(2,2,2-trifluoroethyl)-amino]-methyl}-4-trifluoromethylthiazol-2-yl)-(2,4,6-trichlorophenyl)-amine, Scheme 6 (K)

$^1$H-NMR δ (CDCl$_3$) 3.10 (q, 2H), 3.79 (s, 2H), 4.00 (s, 2H), 7.02 (m, 3H), 7.29 (t, 1H), 7.48 (s, 2H). Mass spec.: 568.01 (MH$^+$).

Example 74

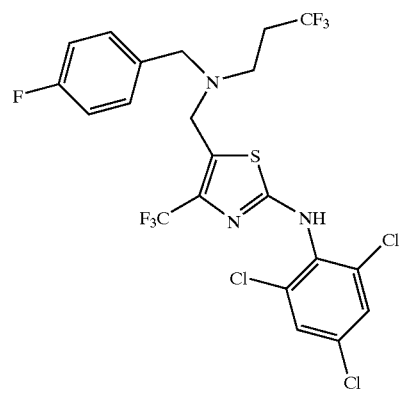

(5-{[(4-Fluorobenzyl)-(3,3,3-trifluoropropyl)-amino]-methyl}-4-trifluoromethylthiazol-2-yl)-(2,4,6-trichlorophenyl)-amine, Scheme 6 (K)

$^1$H-NMR δ (CDCl$_3$) 2.25 (m, 2H), 2.72 (ABq, 2H), 3.52 (s, 2H), 3.71 (s, 2H), 7.00 (t, 2H), 7.23 (ABq, 2H), 7.48 (s, 2H), 7.75 (brs, 1H). Mass spec.: 581.98 (MH$^+$).

Example 75

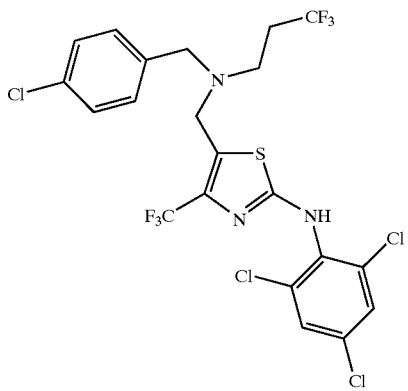

(5-{[(4-Chlorobenzyl)-(3,3,3-trifluoropropyl)-amino]-methyl}-4-trifluoromethylthiazol-2-yl)-(2,4,6-trichlorophenyl)-amine, Scheme 6 (K)

$^1$H-NMR δ (CDCl$_3$) 2.25 (m, 2H), 2.73 (ABq, 2H), 3.57 (s, 2H), 3.71 (s, 2H), 7.24 (q, 4H), 7.48 (s, 2H), 7.91 (brs, 1H). Mass spec.: 598.43 (MH$^+$).

Example 76

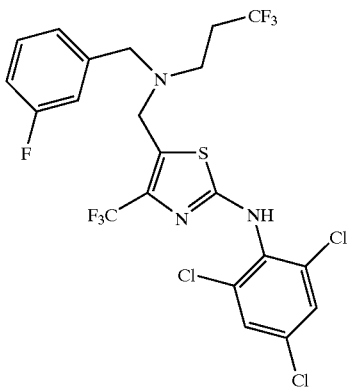

(5-{[(3-Fluorobenzyl)-(3,3,3-trifluoropropyl)-amino]-methyl}-4-trifluoromethylthiazol-2-yl)-(2,4,6-trichlorophenyl)-amine, Scheme 6 (K)

$^1$H-NMR δ (CDCl$_3$) 2.26 (m, 2H), 2.74 (ABq, 2H), 3.60 (s, 2H), 3.73 (s, 2H), 6.99 (m, 3H), 7.27 (t, 1H), 7.49 (s, 2H), 7.84 (brs, 1H). Mass spec.: 582.04 (MH$^+$).

Example 77

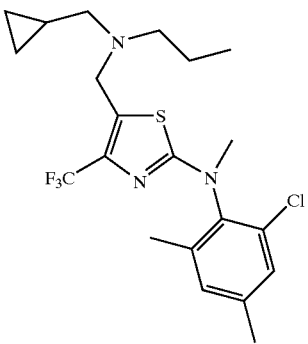

(2-Chloro-4,6-dimethyl-phenyl)-{5-[(cyclopropylmethyl-propyl-amino)-methyl]-4-trifluoromethylthiazol-2-yl}-methyl-amine, Scheme 4 (L)

A solution of (2-chloro-4,6-dimethyl-phenyl)-{5-[(cyclopropylmethyl-propyl-amino)-methyl]-4-trifluoromethylthiazol-2-yl}-amine (157.0 mg, 0.363 mmoles) in tetrahydrofuran (4 mL) at room temperature was treated with a suspension of sodium hydride in mineral oil (60%, 59 mg, 4 equiv.), followed by methyl iodide (0.136 mL, 6 equiv.). The mixture was allowed to stand overnight at room temperature and then the solvents were evaporated. The residue was partitioned between ethyl acetate and water. The organic phase was washed with brine, dried over sodium sulfate and evaporated. The product was purified by chromatography on silica gel, eluting with 10% ethyl acetate/hexane, to give a colorless oil (161.8 mg, 100%). $^1$H-NMR δ (CDCl$_3$) 0.03 (m, 2H), 0.43 (m, 2H), 0.77 (m, 1H), 0.81 (t, 3H), 1.42 (m, 2H), 2.23 (s, 3H), 2.30 (ABq, 2H), 2.33 (s, 3H), 2.46 (ABq, 2H), 3.36 (s, 3H), 3.72 (s, 2H), 7.02 (s, 1H), 7.16 (s, 1H). Mass spec.: 447.16 (MH$^+$).
Similarly prepared using ethyl iodide in place of methyl iodide:

CRF$_1$ Receptor Binding Protocol

CRF$_1$ receptor antagonists, by occupying the same receptors, blocks the accessibility of the receptors to CRF, a hypothalamic factor mediating body's responses to physiological and psychological stress. The following radioligand binding assay examines the ability of the antagonists to bind the CRF$_1$ receptors by assessing their ability to compete with binding of CRF to the receptors in cell membrane.

Compounds of the present invention exemplified in examples 1–14 all showed IC$_{50}$'s less than 75 micromolar. See Table I.

Tissue culture and membrane preparation. IMR-32 cells were grown at 37° C. in 5% CO$_2$ as a monolayer in medium consisting of MEM supplemented with 10% heat-inactivated fetal bovine serum, 0.1 mM nonessential amino acids, 1 mM sodium pyruvate and 2 mM L-glutamine. Cells were transformed by exposure to 2.5 μM 5'-bromo-2'-deoxyuridine for 10 days. After transformation, cells were rinsed twice with phosphate-buffered saline, and incubated for 10–15 min. at 4° C. in homogenization buffer consisting of 50 mM Tris (pH 7.2), 10 mM MgCl$_2$ and 2 mM EGTA. Cells were transferred from plates to polypropylene tubes (16×100 mm), homogenized and centrifuged at 32,000×g for 15 min. Pellets were resuspended by homogenization in buffer and centrifuged at 32,000×g for 15 min. Pellets were resuspended in homogenization buffer then stored at −80° C. until needed.

Radioligand binding assays. Membranes (150 μg /well) were incubated with [$^{125}$I]-oCRF (100 pM) and increasing concentrations of test compound for 100 minutes at 25° C. in a total volume of 200 μl. The assay buffer consisted of 50 mM Tris (pH 7.2), 10 mM MgCl$_2$, 0.5% BSA, 0.005% Triton X-100, 10 μg/ml aprotinin and 10 μg/ml leupeptin. Assays were stopped by addition of ice-cold wash buffer (50 mM Tris, pH 7.4 and 0.2% BSA). Filtration over glass fiber filters (Whatman GF/B) previously soaked in 50 mM Tris, pH 7.2 and 1% BSA was carried out using a Brandel cell harvester. Filters were washed with 10 ml of ice-cold wash buffer. Non-specific binding was defined with 10 μM oCRF. IC$_{50}$ values for oCRF and test compounds were calculated by nonlinear regression using a one-site binding curve (GraphPad Prism).

TABLE I

IC$_{50}$'s of First Set of Examples

| First Set of Examples No. | IC$_{50}$ (CRF-1) |
|---|---|
| 1 | 774 nM |
| 2 | 5.930 uM |
| 3 | 3.660 uM |
| 4 | 1.150 uM |
| 5 | 3.970 uM |
| 6 | 7.010 uM |
| 7 | 71.200 uM |
| 8 | 21.800 uM |
| 9 | 3.700 uM |
| 10 | 15.100 uM |
| 11 | 42.700 uM |
| 12 | 12 nM |
| 13 | 16.600 uM |
| 14 | 19.100 uM |

TABLE 2
IC$_{50}$'s of Compounds from Second Set of Examples
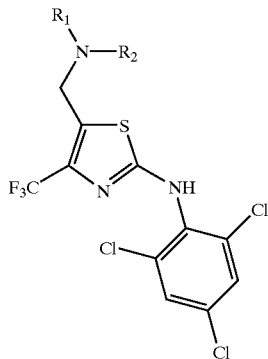
| Example No. | IC$_{50}$, nM |
| --- | --- |
| 1 | 8.6 |
| 2 | 16 |
| 3 | 33 |
| 4 | 37 |
| 5 | 42 |
| 6 | 52 |
| 7 | 54 |
| 8 | 60 |
| 9 | 65 |
| 10 | 68 |
| 11 | 70 |
| 12 | 78 |
| 13 | 80 |
| 14 | 87 |
| 15 | 97 |
| 16 | 103 |
| 17 | 119 |
| 18 | 132 |
| 19 | 132 |
| 20 | 144 |
| 21 | 162 |
| 22 | 178 |
| 23 | 187 |
| 24 | 190 |
| 25 | 212 |
| 26 | 222 |
| 27 | 234 |
| 28 | 236 |
| 29 | 336 |
| 30 | 374 |
| 31 | 410 |
| 32 | 475 |
| 32 | 493 |
| 34 | 511 |
| 35 | 553 |
| 36 | 582 |
| 37 | 629 |
| 38 | 683 |
| 39 | 763 |
| 40 | 781 |
| 41 | 823 |
| 42 | 827 |
| 43 | 1083 |
| 44 | 1152 |
| 45 | 1364 |
| 47 | 1505 |
| 48 | 1529 |
| 49 | 1705 |
| 50 | 2572 |
| 51 | 3792 |
| 52 | 4580 |
| 53 | 4928 |
| 54 | 6272 |
| 55 | 6331 |
| 56 | 6754 |
| 57 | 7069 |
TABLE 2-continued
IC$_{50}$'s of Compounds from Second Set of Examples
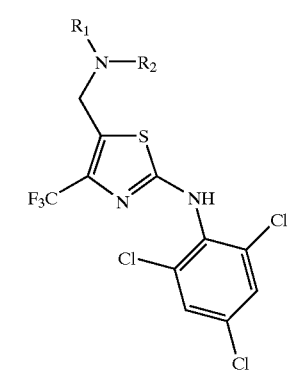
| Example No. | IC$_{50}$, nM |
| --- | --- |
| 58 | 7115 |
| 60 | 8802 |
| 61 | 9408 |
| 62 | 9851 |
| 63 | 35 |
| 64 | 59 |
| 65 | 413 |
| 66 | 1808 |
| 67 | 141 |
| 68 | 39 |
| 69 | 111 |
| 70 | 144 |
| 71 | 226 |
| 72 | 111 |
| 73 | 735 |
| 74 | 6.7 |
| 75 | 4.5 |
| 76 | 5.2 |
TABLE 3
IC$_{50}$'s of Additional Compounds from Second Set of Examples
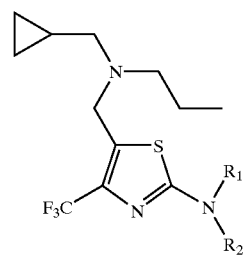
| Example No. | IC$_{50}$, nM |
| --- | --- |
| 77 | 143 |
| 59 | 94 |
| 46 | 79 |
What is claimed is:
1. A compound of Formula (I) or a pharmaceutically acceptable salt or solvate thereof

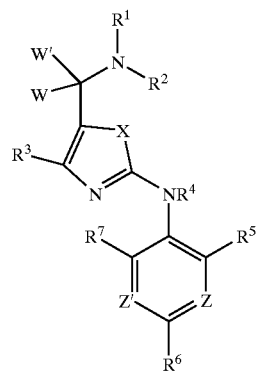

(I)

wherein
X is O, S, NH or N—$C_{1-6}$alkyl;
W and W' are each H;
Z and Z' are independently CH or N
provided that
if Z' is N, then Z is CH;
if Z is N, then Z' is CH;
$R^1$ and $R^2$ are each the same or different and selected from the group consisting of H, $C_{1-6}$alkyl, $C_{1-6}$haloalkyl, $C_{1-6}$alkoxy, $C_{3-7}$cycloalkyl, $C_{1-6}$alkyl-$C_{3-7}$cycloalkyl, $C_{2-6}$alkenyl, $C_{3-6}$alkynyl, $C_{1-6}$cyanoalkyl, $C_{1-6}$aralkyl, 5 or 6-membered heterocycle and 9 or 10-membered bicyclic fused heterocycle;
wherein
said $C_{1-6}$aralkyl is optionally substituted with one or more of the same or different halogens or with one or more of the same or different $C_{1-4}$alkoxy groups;
said 5 or 6-membered heterocycle contains one to three of the same or different heteroatoms selected from the group consisting of O, N and S and said 5 or 6-membered heterocycle is optionally substituted with $C_{1-4}$alkyl, $C_{1-4}$thioalkyl, $C_{1-4}$haloalkyl, halo, cyano or —O—$C_{1-4}$alkyl;
provided that if three of said heteroatoms are contained in said 5-membered heterocycle, said three heteroatoms are not all the same heteroatoms;
said 9 or 10-membered bicyclic fused heterocycle contains one to three of the same or different heteroatoms selected from the group consisting of O, N and S;
$R^1$ and $R^2$ together with the nitrogen to which they are attached form a five or six-membered heterocycle, said heterocycle containing one to three of the same or different heteroatoms selected from the group consisting of N, S or O; and
said heterocycle optionally substituted with one or more $C_{1-6}$alkyl, —$C_{1-6}$alkyl-$C_{1-6}$alkoxy or $C_{1-6}$alkoxy groups;
$R^3$ is $C_{1-6}$alkyl, $C_{1-6}$haloalkyl, halo, cyano or $C_{1-6}$alkoxy;
$R^4$ is H or $C_{1-6}$alkyl;
$R^5$ is H, $C_{1-6}$alkyl or halo;
$R^6$ is $C_{1-6}$alkyl or halo; and
$R^7$ is H, $C_{1-6}$alkyl or halo;
provided that
if $R^5$ is H, then $R^7$ is not H; and
if $R^7$ is H, then $R^5$ is not H.
2. A compound of Formula (I) or a pharmaceutically acceptable salt or solvate thereof

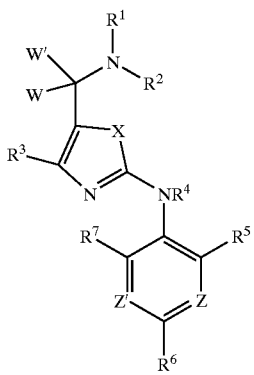

(I)

wherein
X is O, S, NH or N—$C_{1-6}$ alkyl;
W and W' are each H or together are O or S;
Z and Z' are independently CH or N
provided that
if Z' is N, then Z is CH;
if Z is N, then Z' is CH;
$R^1$ and $R^2$ are each the same or different and selected from the group consisting of H, $C_{1-6}$alkyl, $C_{1-6}$haloalkyl, $C_{1-6}$alkoxy, $C_{3-7}$cycloalkyl, $C_{1-6}$alkyl-$C_{3-7}$cycloalkyl, $C_{2-6}$alkenyl, $C_{3-6}$alkynyl, $C_{1-6}$cyanoalkyl, $C_{1-6}$aralkyl, 5 or 6-membered heterocycle and 9 or 10-membered bicyclic fused heterocycle;
wherein
said $C_{1-6}$aralkyl is optionally substituted with one or more of the same or different halogens or with one or more of the same or different $C_{1-4}$alkoxy groups;
said 5 or 6-membered heterocycle contains one to three of the same or different heteroatoms selected from the group consisting of O, N and S and said 5 or 6-membered heterocycle is optionally substituted with $C_{1-4}$alkyl, $C_{1-4}$thioalkyl, $C_{1-4}$haloalkyl, halo, cyano or —O—$C_{1-4}$alkyl;
provided that if three of said heteroatoms are contained in said 5-membered heterocycle, said three heteroatoms are not all the same heteroatoms;
said 9 or 10-membered bicyclic fused heterocycle contains one to three of the same or different heteroatoms selected from the group consisting of O, N and S;
$R^1$ and $R^2$ together with the nitrogen to which they are attached form a five or six-membered heterocycle, said heterocycle containing one to three of the same or different heteroatoms selected from the group consisting of N, S or O; and
said heterocycle optionally substituted with one or more $C_{1-6}$alkyl, —$C_{1-6}$alkyl-$C_{1-6}$alkoxy or $C_{1-6}$alkoxy groups;
$R^3$ is $CF_3$;
$R^4$ is H or $C_{1-6}$alkyl; and
$R^5$, $R^6$ and $R^7$ are each the same or different and selected from the group consisting of
H, $C_{1-6}$alkyl, $C_{1-6}$alkoxy, $C_{1-6}$thioalkyl, CN, $C_{1-6}$haloalkyl and halo.
3. A compound of Formula (I) or a pharmaceutically acceptable salt or solvate thereof

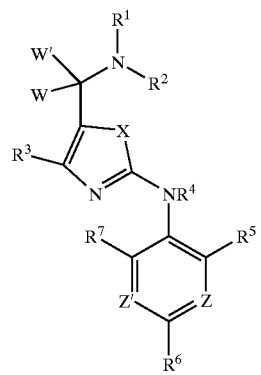

(I)

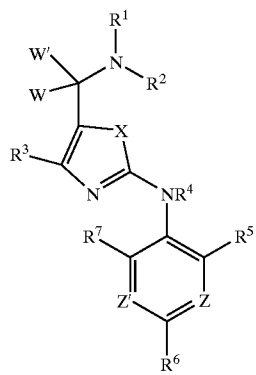

(I)

wherein

X is S;

W and W' are each H or together are O or S;

Z and Z' are independently CH or N
provided that
if Z' is N, then Z is CH;
if Z is N, then Z' is CH;

$R^1$ and $R^2$ are each the same or different and selected from the group consisting of H, $C_{1-6}$alkyl, $C_{1-6}$haloalkyl, $C_{1-6}$alkoxy, $C_{3-7}$cycloalkyl, $C_{1-6}$alkyl-$C_{3-7}$cycloalkyl, $C_{2-6}$alkenyl, $C_{3-6}$alkynyl, $C_{1-6}$cyanoalkyl, $C_{1-6}$aralkyl, 5 or 6-membered heterocycle and 9 or 10-membered bicyclic fused heterocycle;
wherein
said $C_{1-6}$aralkyl is optionally substituted with one or more of the same or different halogens or with one or more of the same or different $C_{1-4}$alkoxy groups;
said 5 or 6-membered heterocycle contains one to three of the same or different heteroatoms selected from the group consisting of O, N and S and said 5 or 6-membered heterocycle is optionally substituted with $C_{1-4}$alkyl, $C_{1-4}$thioalkyl, $C_{1-4}$haloalkyl, halo, cyano or —O—$C_{1-4}$alkyl;
provided that if three of said heteroatoms are contained in said 5-membered heterocycle, said three heteroatoms are not all the same heteroatoms;
said 9 or 10-membered bicyclic fused heterocycle contains one to three of the same or different heteroatoms selected from the group consisting of O, N and S;

$R^1$ and $R^2$ together with the nitrogen to which they are attached form a five or six-membered heterocycle,
said heterocycle containing one to three of the same or different heteroatoms selected from the group consisting of N, S or O; and
said heterocycle optionally substituted with one or more $C_{1-6}$alkyl, —$C_{1-6}$alkyl-$C_{1-6}$alkoxy or $C_{1-6}$alkoxy groups;

$R^3$ is methyl;

$R^4$ is H; and $R^5$, $R^6$ and $R^7$ are each chloro.

4. A compound of Formula (I) or a pharmaceutically acceptable salt or solvate thereof wherein X is S;

W and W' are each H or together are O or S;

Z and Z' are independently CH or N
provided that
if Z' is N, then Z is CH;
if Z is N, then Z' is CH;

$R^1$ and $R^2$ are each the same or different and selected from the group consisting of H, $C_{1-6}$alkyl, $C_{1-6}$haloalkyl, $C_{1-6}$alkoxy, $C_{3-7}$cycloalkyl, $C_{1-6}$alkyl-$C_{3-7}$cycloalkyl, $C_{2-6}$alkenyl, $C_{3-6}$alkynyl, $C_{1-6}$cyanoalkyl, $C_{1-6}$aralkyl, 5 or 6-membered heterocycle and 9 or 10-membered bicyclic fused heterocycle;
wherein
said $C_{1-6}$aralkyl is optionally substituted with one or more of the same or different halogens or with one or more of the same or different $C_{1-4}$alkoxy groups;
said 5 or 6-membered heterocycle contains one to three of the same or different heteroatoms selected from the group consisting of O, N and S and said 5 or 6-membered heterocycle is optionally substituted with $C_{1-4}$alkyl, $C_{1-4}$thioalkyl, $C_{1-4}$haloalkyl, halo, cyano or —O—$C_{1-4}$alkyl;
provided that if three of said heteroatoms are contained in said 5-membered heterocycle, said three heteroatoms are not all the same heteroatoms;
said 9 or 10-membered bicyclic fused heterocycle contains one to three of the same or different heteroatoms selected from the group consisting of O, N and S;

$R^1$ and $R^2$ together with the nitrogen to which they are attached form a five or six-membered heterocycle,
said heterocycle containing one to three of the same or different heteroatoms selected from the group consisting of N, S or O; and
said heterocycle optionally substituted with one or more $C_{1-6}$alkyl, —$C_{1-6}$alkyl-$C_{1-6}$alkoxy or $C_{1-6}$alkoxy groups;

$R^3$ is methyl;

$R^4$ is H; and $R^5$, $R^6$ and $R^7$ are each methyl.

5. A compound of Formula (I) or a pharmaceutically acceptable salt or solvate thereof

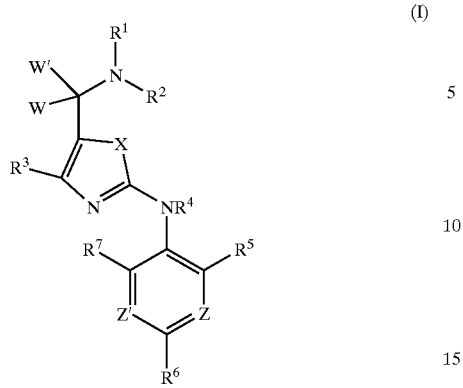

(I)

wherein

X is S;

W and W' are each H;

Z and Z' are independently CH or N provided that
if Z' is N, then Z is CH;
if Z is N, then Z' is CH;

$R^1$ and $R^2$ are each the same or different and selected from the group consisting of H, $C_{1-6}$alkyl, $C_{1-6}$haloalkyl, $C_{1-6}$alkoxy, $C_{3-7}$cycloalkyl, $C_{1-6}$alkyl-$C_{3-7}$cycloalkyl, $C_{2-6}$alkenyl, $C_{3-6}$alkynyl, $C_{1-6}$cyanoalkyl, $C_{1-6}$aralkyl, 5 or 6-membered heterocycle and 9 or 10-membered bicyclic fused heterocycle;

wherein
said $C_{1-6}$aralkyl is optionally substituted with one or more of the same or different halogens or with one or more of the same or different $C_{1-4}$alkoxy groups;
said 5 or 6-membered heterocycle contains one to three of the same or different heteroatoms selected from the group consisting of O, N and S and said 5 or 6-membered heterocycle is optionally substituted with $C_{1-4}$alkyl, $C_{1-4}$thioalkyl, $C_{1-4}$haloalkyl, halo, cyano or —O—$C_{1-4}$alkyl;
provided that if three of said heteroatoms are contained in said 5-membered heterocycle, said three heteroatoms are not all the same heteroatoms;
said 9 or 10-membered bicyclic fused heterocycle contains one to three of the same or different heteroatoms selected from the group consisting of O, N and S;

$R^1$ and $R^2$ together with the nitrogen to which they are attached form a five or six-membered heterocycle, said heterocycle containing one to three of the same or different heteroatoms selected from the group consisting of N, S or O; and
said heterocycle optionally substituted with one or more $C_{1-6}$alkyl, —$C_{1-6}$alkyl-$C_{1-6}$alkoxy or $C_{1-6}$alkoxy groups;

$R^3$ is methyl;

$R^4$ is H; and $R^5$, $R^6$ and $R^7$ are each the same or different and selected from the group consisting of H, $C_{1-6}$alkyl, $C_{1-6}$alkoxy, $C_{1-6}$thioalkyl, CN, $C_{1-6}$haloalkyl and halo.

6. A compound of Formula (I) or a pharmaceutically acceptable salt or solvate thereof

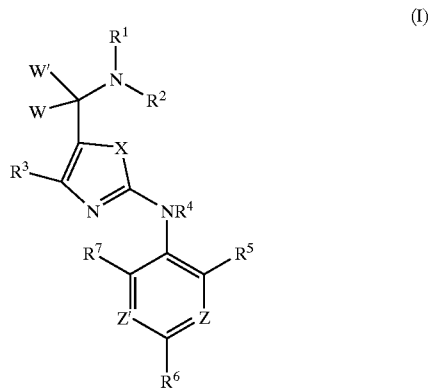

(I)

wherein

X is O, S, NH or N—$C_{1-6}$alkyl;

W and W' are each H or together are O or S;

Z is N;

Z' is CH;

$R^1$ and $R^2$ are each the same or different and selected from the group consisting of H, $C_{1-6}$alkyl, $C_{1-6}$haloalkyl, $C_{1-6}$alkoxy, $C_{3-7}$cycloalkyl, $C_{1-6}$alkyl-$C_{3-7}$cycloalkyl, $C_{2-6}$alkenyl, $C_{3-6}$alkynyl, $C_{1-6}$cyanoalkyl, $C_{1-6}$aralkyl, 5 or 6-membered heterocycle and 9 or 10-membered bicyclic fused heterocycle;

wherein
said $C_{1-6}$aralkyl is optionally substituted with one or more of the same or different halogens or with one or more of the same or different $C_{1-4}$alkoxy groups;
said 5 or 6-membered heterocycle contains one to three of the same or different heteroatoms selected from the group consisting of O, N and S and said 5 or 6-membered heterocycle is optionally substituted with $C_{1-4}$alkyl, $C_{1-4}$thioalkyl, $C_{1-4}$haloalkyl, halo, cyano or —O—$C_{1-4}$alkyl;
provided that if three of said heteroatoms are contained in said 5-membered heterocycle, said three heteroatoms are not all the same heteroatoms;
said 9 or 10-membered bicyclic fused heterocycle contains one to three of the same or different heteroatoms selected from the group consisting of O, N and S;

$R^1$ and $R^2$ together with the nitrogen to which they are attached form a five or six-membered heterocycle, said heterocycle containing one to three of the same or different heteroatoms selected from the group consisting of N, S or O; and
said heterocycle optionally substituted with one or more $C_{1-6}$alkyl, —$C_{1-6}$alkyl-$C_{1-6}$alkoxy or $C_{1-6}$alkoxy groups;

$R^3$ is $C_{1-6}$alkyl, $C_{1-6}$haloalkyl, halo, cyano or $C_{1-6}$alkoxy;

$R^4$ is H or $C_{1-6}$alkyl; and $R^5$, $R^6$ and $R^7$ are each the same or different and selected from the group consisting of H, $C_{1-6}$alkyl, $C_{1-6}$alkoxy, $C_{1-6}$thioalkyl, CN, $C_{1-6}$haloalkyl and halo.

7. A compound of Formula (I) or a pharmaceutically acceptable salt or solvate thereof

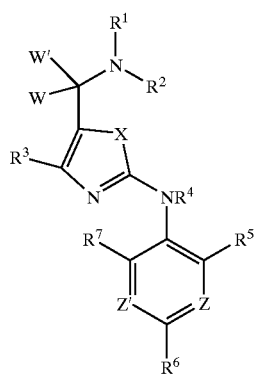

(I)

wherein
X is O, S, NH or N—$C_{1-6}$alkyl;
W and W' are each H or together are O or S;
Z is CH;
Z' is N;
$R^1$ and $R^2$ are each the same or different and selected from the group consisting of H, $C_{1-6}$alkyl, $C_{1-6}$haloalkyl, $C_{1-6}$alkoxy, $C_{3-7}$cycloalkyl, $C_{1-6}$alkyl-$C_{3-7}$cycloalkyl, $C_{2-6}$alkenyl, $C_{3-6}$alkynyl, $C_{1-6}$cyanoalkyl, $C_{1-6}$aralkyl, 5 or 6-membered heterocycle and 9 or 10-membered bicyclic fused heterocycle;
wherein
said $C_{1-6}$aralkyl is optionally substituted with one or more of the same or different halogens or with one or more of the same or different $C_{1-4}$alkoxy groups;
said 5 or 6-membered heterocycle contains one to three of the same or different heteroatoms selected from the group consisting of O, N and S and said 5 or 6-membered heterocycle is optionally substituted with $C_{1-4}$alkyl, $C_{1-4}$thioalkyl, $C_{1-4}$haloalkyl, halo, cyano or —O—$C_{1-4}$alkyl;
provided that if three of said heteroatoms are contained in said 5-membered heterocycle, said three heteroatoms are not all the same heteroatoms;
said 9 or 10-membered bicyclic fused heterocycle contains one to three of the same or different heteroatoms selected from the group consisting of O, N and S;
$R^1$ and $R^2$ together with the nitrogen to which they are attached form a five or six-membered heterocycle, said heterocycle containing one to three of the same or different heteroatoms selected from the group consisting of N, S or O; and
said heterocycle optionally substituted with one or more $C_{1-6}$alkyl, —$C_{1-6}$alkyl-$C_{1-6}$alkoxy or $C_{1-6}$alkoxy groups;
$R^3$ is $C_{1-6}$alkyl, $C_{1-6}$haloalkyl, halo, cyano or $C_{1-6}$alkoxy;
$R^4$ is H or $C_{1-6}$alkyl; and
$R^5$, $R^6$ and $R^7$ are each the same or different and selected from the group consisting of H, $C_{1-6}$alkyl, $C_{1-6}$alkoxy, $C_{1-6}$thioalkyl, CN, $C_{1-6}$haloalkyl and halo.

8. A method of treating depression, anxiety, affective disorders, feeding disorders, post-traumatic stress disorder, headache, drug addiction and drug or alcohol withdrawal symptoms comprising the administration of a compound of Formula (I) or a pharmaceutically acceptable salt or solvate thereof

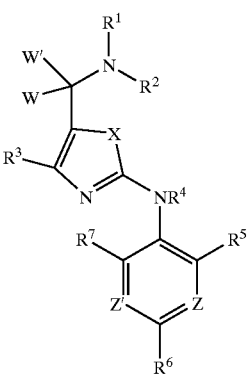

(I)

wherein
X is O, S, NH or N—$C_{1-6}$alkyl;
W and W' are each H or together are O or S;
Z and Z' are independently CH or N
provided that
if Z' is N, then Z is CH;
if Z is N, then Z' is CH;
$R^1$ and $R^2$ are each the same or different and selected from the group consisting of H, $C_{1-6}$alkyl, $C_{1-6}$haloalkyl, $C_{1-6}$alkoxy, $C_{3-7}$cycloalkyl, $C_{1-6}$alkyl-$C_{3-7}$cycloalkyl, $C_{2-6}$alkenyl, $C_{3-6}$alkynyl, $C_{1-6}$cyanoalkyl, $C_{1-6}$aralkyl, 5 or 6-membered heterocycle and 9 or 10-membered bicyclic fused heterocycle;
wherein
said $C_{1-6}$aralkyl is optionally substituted with one or more of the same or different halogens or with one or more of the same or different $C_{1-4}$alkoxy groups;
said 5 or 6-membered heterocycle contains one to three of the same or different heteroatoms selected from the group consisting of O, N and S and said 5 or 6-membered heterocycle is optionally substituted with $C_{1-4}$alkyl, $C_{1-4}$thioalkyl, $C_{1-4}$haloalkyl, halo, cyano or —O—$C_{1-4}$alkyl;
provided that if three of said heteroatoms are contained in said 5-membered heterocycle, said three heteroatoms are not all the same heteroatoms;
said 9 or 10-membered bicyclic fused heterocycle contains one to three of the same or different heteroatoms selected from the group consisting of O, N and S;
$R^1$ and $R^2$ together with the nitrogen to which they are attached form a five or six-membered heterocycle, said heterocycle containing one to three of the same or different heteroatoms selected from the group consisting of N, S or O; and
said heterocycle optionally substituted with one or more $C_{1-6}$alkyl, —$C_{1-6}$alkyl-$C_{1-6}$alkoxy or $C_{1-6}$alkoxy groups;
$R^3$ is $C_{1-6}$alkyl, $C_{1-6}$haloalkyl, halo, cyano or $C_{1-6}$alkoxy;
$R^4$ is H or $C_{1-6}$alkyl; and
$R^5$, $R^6$ and $R^7$ are each the same or different and selected from the group consisting of H, $C_{1-6}$alkyl, $C_{1-6}$alkoxy, $C_{1-6}$thioalkyl, CN, $C_{1-6}$haloalkyl and halo.

9. A method of treating depression comprising the administration of a compound of Formula (I) or a pharmaceutically acceptable salt or solvate thereof

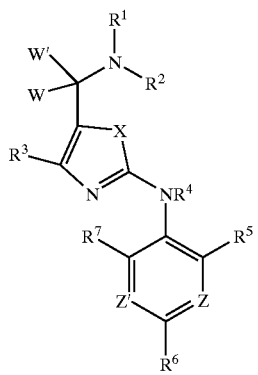

(I)

wherein
X is O, S, NH or N—$C_{1-6}$alkyl;
W and W' are each H or together are O or S;
Z and Z' are independently CH or N
provided that
if Z' is N, then Z is CH;
if Z is N, then Z' is CH;
$R^1$ and $R^2$ are each the same or different and selected from the group consisting of H, $C_{1-6}$alkyl, $C_{1-6}$haloalkyl, $C_{1-6}$alkoxy, $C_{3-7}$cycloalkyl, $C_{1-6}$alkyl-$C_{3-7}$cycloalkyl, $C_{2-6}$alkenyl, $C_{3-6}$alkynyl, $C_{1-6}$cyanoalkyl, $C_{1-6}$aralkyl, 5 or 6-membered heterocycle and 9 or 10-membered bicyclic fused heterocycle;
wherein
said $C_{1-6}$aralkyl is optionally substituted with one or more of the same or different halogens or with one or more of the same or different $C_{1-4}$alkoxy groups;
said 5 or 6-membered heterocycle contains one to three of the same or different heteroatoms selected from the group consisting of O, N and S and said 5 or 6-membered heterocycle is optionally substituted with $C_{1-4}$alkyl, $C_{1-4}$thioalkyl, $C_{1-4}$haloalkyl, halo, cyano or —O—$C_{1-4}$alkyl;
provided that if three of said heteroatoms are contained in said 5-membered heterocycle, said three heteroatoms are not all the same heteroatoms;
said 9 or 10-membered bicyclic fused heterocycle contains one to three of the same or different heteroatoms selected from the group consisting of O, N and S;
$R^1$ and $R^2$ together with the nitrogen to which they are attached form a five or six-membered heterocycle, said heterocycle containing one to three of the same or different heteroatoms selected from the group consisting of N, S or O; and
said heterocycle optionally substituted with one or more $C_{1-6}$alkyl, —$C_{1-6}$alkyl-$C_{1-6}$alkoxy or $C_{1-6}$alkoxy groups;
$R^3$ is $C_{1-6}$-alkyl, $C_{1-6}$haloalkyl, halo, cyano or $C_{1-6}$alkoxy;
$R^4$ is H or $C_{1-6}$alkyl; and
$R^5$, $R^6$ and $R^7$ are each the same or different and selected from the group consisting of H, $C_{1-6}$alkyl, $C_{1-6}$alkoxy, $C_{1-6}$thioalkyl, CN, $C_{1-6}$haloalkyl and halo.

10. A compound according to claim 1 wherein said 5 or 6-membered heterocycle is pyridyl, pryrimidinyl, thienyl, imidazolyl, $C_{1-3}$thioalkyl-subsituted thiadiazolyl, pyrrolyl, pyrrolinyl, pyrrolidinyl, thiazolyl, oxazolyl or furanyl.

11. A compound according to claim 1 wherein said 9 or 10-membered bicyclic fused heterocycle is benzofuranyl, indolyl, benzothiazolyl or benzimidazolyl.

12. A compound according to claim 1 wherein $R^1$ is not H and $R^2$ is not H.

13. A compound according to claim 1 wherein the optionally substituted heterocycle formed by $R^1$ and $R^2$ together with the nitrogen to which they are attached is selected from the group consisting of pyrrolyl, pyrrolinyl, pyrrolidinyl, piperidinyl, piperazinyl, morpholinyl, imidazolyl and thiomorpholinyl.

14. A compound according to claim 1 wherein $R^1$ and $R^2$ are each the same or different and selected from the group consisting of H, methyl, ethyl, propyl, isopropyl, cyclopropyl, propenyl, cyclopropylmethyl, butyl, n-butyl, sec-butyl, tert-butyl, cyclobutyl, pentyl, $(CH_2)_2CF_3$, $(CH_2)_2OCH_3$, $CH_2CH(CH_2CH_3)_2$, $CH_2CH(CH_2CH_3)(OCH_3)$, $CH_2CH(CH_3)_2$, $CH(CH_3)(CH_2CH_3)$, $CH_2CCH$, $CH_2CN$, $CH_2C(CH_2)(CH_3)$, $(CH_2)_2CN$, phenyl, methylphenyl, ethylphenyl, cyclobutylmethyl and propylphenyl.

15. A compound according to claim 1 wherein $R^4$ is H.

16. A compound according to claim 1 wherein $R^4$ is $CH_3$ or $CH_2CH_3$.

17. A compound according to claim 1 wherein X is S.

18. A compound or pharmaceutically acceptable salt or solvate thereof selected from the group consisting of 2-(2,4,6-Trimethylphenylamino)-5-(N-n-propyl-N-cyclopropylmethyl)aminomethyl-4-trifluoromethylthiazole; 2-(2-Chloro-4,6-dimethylphenylamino)-5-(N-n-propyl-N-cyclopropylmethyl)aminomethyl-4-trifluoromethylthiazole; 2-(2,4,6-Trichlorophenylamino)-5-(N-n-butyl-N-ethyl)aminomethyl-4-trifluoromethylthiazole; 2-(2,4,6-Trimethylphenylamino)-5-(N-n-butyl-N-ethyl)aminomethyl-4-trifluoromethylthiazole; 2-(2-Chloro-4,6-dimethylphenylamino)-5-(N-n-butyl-N-ethyl)aminomethyl-4-trifluoromethylthiazole; 2-(2,4,6-Trichlorophenylamino)-5-(N,N-bis-n-propyl)aminomethyl-4-trifluoromethylthiazole; 2-(2,4,6-Trimethylphenylamino)-5-(N,N-bis-n-propyl)aminomethyl-4-trifluoromethylthiazole; 2-(2-Chloro-4,6-dimethylphenylamino)-5-(N,N-bis-n-propyl)aminomethyl-4-trifluoromethylthiazole; 2-(2,4,6-Trichlorophenylamino)-5-(N,N-bis-2-methoxyethyl)aminomethyl-4-trifluoromethylthiazole; 2-(2,4,6-Trimethylphenylamino)-5-(N,N-bis-2-methoxyethyl)aminomethyl-4-trifluoromethylthiazole; 2-(2-Chloro-4,6-dimethylphenylamino)-5-(N,N-bis-2-methoxyethyl)aminomethyl-4-trifluoromethylthiazole; 2-(2,4,6-Trichlorophenylamino)-5-(N-2-methoxyethyl-N-ethyl)arninomethyl-4-trifluoromethylthiazole; 2-(2,4,6-Trimethylphenylamino)-5-(N-2-methoxyethyl-N-ethyl)aminomethyl-4-trifluoromethylthiazole; 2-(2-Chloro-4,6-dimethylphenylamino)-5-(N-2-methoxyethyl-N-ethyl)aminomethyl-4-trifluoromethylthiazole; 2-(2,4,6-Trichlorophenylamino)-5-(N-n-propyl-N-cyclopropylmethyl)aminomethyl-4-trifluoromethyloxazole; 2-(2,4,6-Trimethylphenylamino)-5-(N-n-propyl-N-cyclopropylmethyl)aminomethyl-4-trifluoromethyloxazole; 2-(2-Chloro-4,6-dimethylphenylamino)-5-(N-n-propyl-N-cyclopropylmethyl)aminomethyl-4-trifluoromethyloxazole; 2-(2,4,6-Trichlorophenylamino)-5-(N-n-butyl-N-ethyl)aminomethyl-4-trifluoromethyloxazole; 2-(2,4,6-Trimethylphenylamino)-5-(N-n-butyl-N-ethyl)aminomethyl-4-trifluoromethyloxazole; 2-(2-Chloro-4,6-dimethylphenylamino)-5-(N-n-butyl-N-ethyl)aminomethyl-4-trifluoromethyloxazole; 2-(2,4,6-Trichlorophenylamino)-5-(N,N-bis-n-propyl)aminomethyl-4-trifluoromethyloxazole; 2-(2,4,6-Trimethylphenylamino)-5-(N,N-bis-n-propyl)aminomethyl-4-trifluoromethyloxazole; 2-(2-Chloro-4,6-dimethylphenylamino)-5-(N,N-bis-n-propyl)aminomethyl-4-trifluoromethyloxazole; 2-(2,4,6-

Trichlorophenylamino)-5-(N,N-bis-2-methoxyethyl) aminomethyl-4-trifluoromethyloxazole; 2-(2,4,6-Trimethylphenylamino)-5-(N,N-bis-2-methoxyethyl) amninomethyl-4-trifluoromethyloxazole; 2-(2-Chloro-4,6-dimethylphenylamino)-5-(N,N-bis-2-methoxyethyl) aminomethyl-4-trifluoromethyloxazole; 2-(2,4,6-Trichlorophenylamino)-5-(N-2-methoxyethyl-N-ethyl) aminomethyl-4-trifluoromethyloxazole; 2-(2,4,6-Trimethylphenylamino)-5-(N-2-methoxyethyl-N-ethyl) aminomethyl-4-trifluoromethyloxazole; 2-(2,4,6-Trichlorophenylamino)-5-(N-n-propyl-N-cyclopropylmethyl)aminomethyl-4-trifluoromethylthiazole and 2-(2-Chloro-4,6-dimethylphenylamino)-5-(N-2-methoxyethyl-N-ethyl)aminomethyl-4-trifluoromethyloxazole.

19. A compound or pharmaceutically acceptable salt or solvate thereof selected from the group consisting of (5-{[(4-Chlorobenzyl)-propyl-amino]-methyl}-4-trifluoromethylthiazol-2-yl)-(2,4,6-trichlorophenyl)-amine; (5-{[(3-Fluorobenzyl)-(3,3,3-trifluoropropyl)-amino]-methyl}-4-trifluoromethylthiazol-2-yl)-(2,4,6-trichlorophenyl)-amine; (5-{[(4-Fluorobenzyl)-(3,3,3-trifluoropropyl)-amino]-methyl}-4-trifluoromethylthiazol-2-yl)-(2,4,6-trichlorophenyl)-amine and (5-{[Benzyl-(3,3,3-trifluoropropyl)-amino]-methyl}-4-trifluoromethylthiazol-2-yl)-(2,4,6-trichlorophenyl)-amine.

20. A compound or pharmaceutically acceptable salt or solvate thereof selected from the group consisting of (5-{[Benzyl-(3,3,3-trifluoropropyl)-amino]-methyl}-4-trifluoromethylthiazol-2-yl)-(2,4,6-trichlorophenyl)-amine; (5-{[(4-Chlorobenzyl)-propyl-amino]-methyl}-4-trifluoromethylthiazol-2-yl)-(2,4,6-trichlorophenyl)-amine; {5-[(Cyclopropylmethyl-ethyl-amino)-methyl]-4-trifluoromethyl-thiazol-2-yl}-(2,4,6-trichloro-phenyl)-amine; {5-[(Bis-cyclopropylmethyl-amino)-methyl]-4-trifluoromethyl-thiazol-2-yl}-(2,4,6-trichloro-phenyl)-amine; (5-{[(3,4-Dichloro-benzyl)-propyl-amino]-methyl}-4-trifluoromethyl-thiazol-2-yl)-(2,4,6-trichloro-phenyl)-amine (5-{[(4-Methoxy-benzyl)-propyl-amino]-methyl}-4-trifluoromethyl-thiazol-2-yl)-(2,4,6-trichloro-phenyl)-amine; {5-[(Benzyl-propyl-amino)-methyl]-4-trifluoromethyl-thiazol-2-yl}-(2,4,6-trichloro-phenyl)-amine; (5-{[Cyclopropylmethyl-(2,2,2-trifluoro-ethyl)-amino]-methyl}-4-trifluoromethyl-thiazol-2-yl)-(2,4,6-trichloro-phenyl)-amine; (5-{[Cyclopropylmethyl-(3,3,3-trifluoro-propyl)-amino]-methyl}-4-trifluoromethyl-thiazol-2-yl)-(2,4,6-trichloro-phenyl)-amine; {5-[(Allyl-cyclopropylmethyl-amino)-methyl]-4-trifluoromethyl-thiazol-2-yl}-(2,4,6-trichloro-phenyl)-amine; (5-{[Phenethyl-(2,2,2-trifluoro-ethyl)-amino]-methyl}-4-trifluoromethyl-thiazol-2-yl)-(2,4,6-trichloro-phenyl)-amine; (5-{[(3,4-Difluoro-benzyl)-propyl-amino]-methyl}-4-trifluoromethyl-thiazol-2-yl)-(2,4,6-trichloro-phenyl)-amine; (5-Diallylaminomethyl-4-trifluoromethyl-thiazol-2-yl)-(2,4,6-trichloro-phenyl)-amine; (2,4,6-Trichloro-phenyl)-(5-{[(2,2,2-trifluoro-ethyl)-(3,3,3-trifluoro-propyl)-amino]-methyl}-4-trifluoromethyl-thiazol-2-yl)-amine; [5-({[2-(3,4-Dichloro-phenyl)-ethyl]-propyl-amino}-methyl)-4-trifluoromethyl-thiazol-2-yl]-(2,4,6-trichloro-phenyl)-amine; {5-[(Cyclobutylmethyl-propyl-amino)-methyl]-4-trifluoromethyl-thiazol-2-yl}-(2,4,6-trichloro-phenyl)-amine; {5-[(Cyclopropylmethyl-prop-2-ynyl-amino)-methyl]-4-trifluoromethyl-thiazol-2-yl}-(2,4,6-trichloro-phenyl)-amine; (5-{[Cyclobutylmethyl-(2,2,2-trifluoro-ethyl)-amino]-methyl}-4-trifluoromethyl-thiazol-2-yl)-(2,4,6-trichloro-phenyl)-amine; {5-[(Benzo[1,3]dioxol-5-ylmethyl-propyl-amino)-methyl]-4-trifluoromethyl-thiazol-2-yl}-(2,4,6-trichloro-phenyl)-amine; (5-{[Propyl-(3,3,3-trifluoro-propyl)-amino]-methyl}-4-trifluoromethyl-thiazol-2-yl)-(2,4,6-trichloro-phenyl)-amine; {5-[(Benzyl-ethyl-amino)-methyl]-4-trifluoromethyl-thiazol-2-yl}-(2,4,6-trichloro-phenyl)-amine; {5-[(Propyl-thiophen-2-ylmethyl-amino)-methyl]-4-trifluoromethyl-thiazol-2-yl}-(2,4,6-trichloro-phenyl)-amine; (5-{[Phenethyl-(3,3,3-trifluoro-propyl)-amino]-methyl}-4-trifluoromethyl-thiazol-2-yl)-(2,4,6-trichloro-phenyl)-amine; (5-{[Propyl-(2,2,2-trifluoro-ethyl)-amino]-methyl}-4-trifluoromethyl-thiazol-2-yl)-(2,4,6-trichloro-phenyl)-amine; {5-[(Ethyl-propyl-amino)-methyl]-4-trifluoromethyl-thiazol-2-yl}-(2,4,6-trichloro-phenyl)-amine; (5-Dipropylaminomethyl-4-trifluoromethyl-thiazol-2-yl)-(2,4,6-trichloro-phenyl)-amine; (5-{[Cyclopropylmethyl-(2,2,3,3,3-pentafluoro-propyl)-amino]-methyl}-4-trifluoromethyl-thiazol-2-yl)-(2,4,6-trichloro-phenyl)-amine; (5-{[(2-Cyclopropyl-ethyl)-(2,2,2-trifluoro-ethyl)-amino]-methyl}-4-trifluoromethyl-thiazol-2-yl)-(2,4,6-trichloro-phenyl)-amine; {5-[(Isobutyl-propyl-amino)-methyl]-4-trifluoromethyl-thiazol-2-yl}-(2,4,6-trichloro-phenyl)-amine; 3-{Butyl-[2-(2,4,6-trichloro-phenylamino)-4-trifluoromethyl-thiazol-5-ylmethyl]-amino}-propionitrile; {5-[(Butyl-ethyl-amino)-methyl]-4-trifluoromethyl-thiazol-2-yl}-(2,4,6-trichloro-phenyl)-amine; (5-Diethylaminomethyl-4-trifluoromethyl-thiazol-2-yl)-(2,4,6-trichloro-phenyl)-amine; (5-{[Ethyl-(2-methyl-allyl)-amino]-methyl}-4-trifluoromethyl-thiazol-2-yl)-(2,4,6-trichloro-phenyl)-amine {5-[(Ethyl-pyridin-4-ylmethyl-amino)-methyl]-4-trifluoromethyl-thiazol-2-yl}-(2,4,6-trichloro-phenyl)-amine (5-{[Benzyl-(2,2,2-trifluoro-ethyl)-amino]-methyl}-4-trifluoromethyl-thiazol-2-yl)-(2,4,6-trichloro-phenyl)-amine; (5-{[(2-Cyclopropyl-ethyl)-propyl-amino]-methyl}-4-trifluoromethyl-thiazol-2-yl)-(2,4,6-trichloro-phenyl)-amine; (5-{[Ethyl-(2-methoxy-ethyl)-amino]-methyl}-4-trifluoromethyl-thiazol-2-yl)-(2,4,6-trichloro-phenyl)-amine; {5-[(Diisobutylamino)-methyl]-4-trifluoromethyl-thiazol-2-yl}-(2,4,6-trichloro-phenyl)-amine; {Butyl-[2-(2,4,6-trichloro-phenylamino)-4-trifluoromethyl-thiazol-5-ylmethyl]-amino}-acetonitrile; {5-[(Methyl-phenethyl-amino)-methyl]-4-trifluoromethyl-thiazol-2-yl}-(2,4,6-trichloro-phenyl)-amine; (5-{[(2,2,3,3,3-Pentafluoro-propyl)-propyl-amino]-methyl}-4-trifluoromethyl-thiazol-2-yl)-(2,4,6-trichloro-phenyl)-amine; (5-{[Bis-(2-methyl-allyl)-amino]-methyl}-4-trifluoromethyl-thiazol-2-yl)-(2,4,6-trichloro-phenyl)-amine; {5-[(Furan-2-ylmethyl-propyl-amino)-methyl]-4-trifluoromethyl-thiazol-2-yl}-(2,4,6-trichloro-phenyl)-amine; (5-{[(2-Cyclopropyl-ethyl)-(3,3,3-trifluoro-propyl)-amino]-methyl}-4-trifluoromethyl-thiazol-2-yl)-(2,4,6-trichloro-phenyl)-amine; {5-[(Isobutyl-methyl-amino)-methyl]-4-trifluoromethyl-thiazol-2-yl}-(2,4,6-trichloro-phenyl)-amine; {5-[(Isobutyl-methyl-amino)-methyl]-4-trifluoromethyl-thiazol-2-yl}-(2,4,6-trichloro-phenyl)-amine; (5-{[(2-Cyclopropyl-ethyl)-ethyl-amino]-methyl}-4-trifluoromethyl-thiazol-2-yl)-(2,4,6-trichloro-phenyl)-amine; (5-Methylsulfanyl-[1,3,4]thiadiazol-2-yl)-[2-(2,4,6-trichloro-phenylamino)-4-trifluoromethyl-thiazol-5-ylmethyl]-amine; {5-[(Ethyl-methyl-amino)-methyl]-4-trifluoromethyl-thiazol-2-yl}-(2,4,6-trichloro-phenyl)-amine; [5-(2-Ethyl-imidazol-1-ylmethyl)-4-trifluoromethyl-thiazol-2-yl]-(2,4,6-trichloro-phenyl)-amine; (5-{[2-(3,4-Dichloro-phenyl)-ethylamino]-methyl}-4-trifluoromethyl-thiazol-2-yl)-(2,4,6-trichloro-phenyl)-amine; {5-[(Butyl-methyl-amino)-methyl]-4-trifluoromethyl-thiazol-2-yl}-(2,4,6-trichloro-phenyl)-amine; (2,4,6-Trichloro-phenyl)-(4-trifluoromethyl-5-{[2-(3-trifluoromethyl-phenyl)-ethylamino]-methyl}-thiazol-2-yl)-amine; {5-[(4-Chlorobenzylamino)-methyl]-4-trifluoromethyl-thiazol-2-yl}-(2,4,6-trichloro-phenyl)-amine; (5-{[Bis-(2-methoxy-ethyl)-amino]-methyl}-4-trifluoromethyl-thiazol-2-yl)-(2,4,6-trichloro-phenyl)-amine; {5-[(Methyl-pentyl-amino)-methyl]-4-trifluoromethyl-thiazol-2-yl}-(2,4,6-trichloro-phenyl)-amine; {5-[(3,4-Dichloro-benzylamino)-methyl]-4-trifluoromethyl-thiazol-2-yl}-(2,4,6-trichloro-phenyl)-amine; [5-(2-Methoxymethyl-pyrrolidin-1-ylmethyl)-4-trifluoromethyl-thiazol-2-yl]-(2,4,6-trichloro-phenyl)-amine; (5-{[2-(4-Chloro-phenyl)-ethylamino]-methyl}-4-trifluoromethyl-thiazol-2-yl)-(2,4,6-trichloro-phenyl)-amine; {5-[(Cyclohexylmethyl-propyl-amino)-methyl]-4-trifluoromethyl-thiazol-2-yl}-(2,4,6-trichloro-phenyl)-amine; [5-(2,5-Dihydro-pyrrol-1-ylmethyl)-4-trifluoromethyl-thiazol-2-yl]-(2,4,6-trichloro-phenyl)-amine; (5-{[2-(3-Fluoro-phenyl)-ethylamino]-methyl}-4-trifluoromethyl-thiazol-2-yl)-(2,4,6-trichloro-phenyl)-amine; (5-{[(4-Fluorobenzyl)-propyl-amino]-methyl}-4-trifluoromethylthiazol-2-yl)-(2,4,6-trichlorophenyl)-amine; (5-{[(3-Fluorobenzyl)-propyl-amino]-methyl}-4-trifluoromethylthiazol-2-yl)-(2,4,6-trichlorophenyl)-amine; {5-[(Propyl-pyridin-3-ylmethyl-amino)-methyl]-4-trifluoromethylthiazol-2-yl}-(2,4,6-trichloro-phenyl)-amine; {5-[(Propyl-pyridin-2-ylmethyl-amino)-methyl]-4-trifluoromethylthiazol-2-yl}-(2,4,6-trichlorophenyl)-amine; {5-[(Propyl-pyridin-4-ylmethyl-amino)-methyl]-4-trifluoromethylthiazol-2-yl}-(2,4,6-trichlorophenyl)-amine; {5-[(Phenethyl-propyl-amino)-methyl]-4-trifluoromethylthiazol-2-yl}-(2,4,6-trichlorophenyl)-amine; {5-[(Phenethyl-ethyl-amino)-methyl]-4-trifluoromethylthiazol-2-yl}-(2,4,6-trichlorophenyl)-amine; {5-[(Allyl-propyl-amino)-methyl]-4-trifluoromethylthiazol-2-yl}-(2,4,6-trichlorophenyl)-amine; (5-{[(4-Fluorobenzyl)-(2,2,2-trifluoroethyl)-amino]-methyl}-4-trifluoromethylthiazol-2-yl)-(2,4,6-trichlorophenyl)-amine; (5-{[(4-Chlorobenzyl)-(2,2,2-trifluoroethyl)-amino]-methyl}-4-trifluoromethylthiazol-2-yl)-(2,4,6-trichlorophenyl)-amine; (5-{[(3-Fluorobenzyl)-(2,2,2-trifluoroethyl)-amino]-methyl}-4-trifluoromethylthiazol-2-yl)-(2,4,6-trichlorophenyl)-amine; (5-{[(4-Fluorobenzyl)-(3,3,3-trifluoropropyl)-amino]-methyl}-4-trifluoromethylthiazol-2-yl)-(2,4,6-trichlorophenyl)-amine; (5-{[(4-Chlorobenzyl)-(3,3,3-trifluoropropyl)-amino]-methyl}-4-trifluoromethylthiazol-2-yl)-(2,4,6-trichlorophenyl)-amine; (5-{[(3-Fluorobenzyl)-(3,3,3-trifluoropropyl)-amino]-methyl}-4-trifluoromethylthiazol-2-yl)-(2,4,6-trichlorophenyl)-amine; (2-Chloro-4,6-dimethyl-phenyl)-{5-[(cyclopropylmethyl-propyl-amino)-methyl]-4-trifluoromethylthiazol-2-yl}-methyl-amine; (2-Chloro-4,6-dimethyl-phenyl)-{5-[(cyclopropylmethyl-propyl-amino)-methyl]-4-trifluoromethylthiazol-2-yl}-ethyl-amine; and (2-Bromo-4-isopropyl-phenyl)-{5-[(cyclopropylmethyl-propyl-amino)-methyl]-4-trifluoromethylthiazol-2-yl}-ethyl-amine.

21. A pharmaceutical composition comprising a compound according to claim 1.

\* \* \* \* \*